United States Patent
Oh et al.

(10) Patent No.: US 11,971,357 B2
(45) Date of Patent: Apr. 30, 2024

(54) IN SITU MEASUREMENT OF ABSOLUTE CONCENTRATIONS BY NORMALIZED RAMAN IMAGING

(71) Applicant: PRESIDENT AND FELLOWS OF HARVARD COLLEGE, Cambridge, MA (US)

(72) Inventors: Seungeun Oh, Cambridge, MA (US); Marc Kirschner, Cambridge, MA (US)

(73) Assignee: PRESIDENT AND FELLOWS OF HARVARD COLLEGE, Cambridge, MA (US)

(*) Notice: Subject to any disclaimer, the term of this patent is extended or adjusted under 35 U.S.C. 154(b) by 233 days.

(21) Appl. No.: 17/594,353

(22) PCT Filed: May 7, 2020

(86) PCT No.: PCT/US2020/031943
§ 371 (c)(1),
(2) Date: Oct. 12, 2021

(87) PCT Pub. No.: WO2020/227571
PCT Pub. Date: Nov. 12, 2020

(65) Prior Publication Data
US 2022/0187209 A1   Jun. 16, 2022

Related U.S. Application Data

(60) Provisional application No. 62/844,320, filed on May 7, 2019.

(51) Int. Cl.
*G01J 3/44* (2006.01)
*G01N 21/65* (2006.01)
*G01N 33/68* (2006.01)
*G01N 33/92* (2006.01)

(52) U.S. Cl.
CPC ....... *G01N 21/65* (2013.01); *G01N 2021/655* (2013.01); *G01N 33/68* (2013.01); *G01N 33/92* (2013.01)

(58) Field of Classification Search
CPC ........ G01N 21/65; G01N 33/68; G01N 33/92; G01N 2021/655; G01J 3/44
See application file for complete search history.

(56) References Cited

U.S. PATENT DOCUMENTS

| | | | |
|---|---|---|---|
| 2009/0270702 A1 | 10/2009 | Zeng et al. | |
| 2010/0046039 A1 | 2/2010 | Xie et al. | |
| 2014/0336261 A1* | 11/2014 | Chin | A61B 5/0073 514/604 |

(Continued)

OTHER PUBLICATIONS

Ginzberg, M. B., Kafri, R. & Kirschner, M. On being the right (cell) size. Science (80-.). 348, 1245075-1245075 (2015) (9 pages).

(Continued)

*Primary Examiner* — Abdullahi Nur
(74) *Attorney, Agent, or Firm* — NIXON PEABODY LLP

(57) ABSTRACT

A method for measuring a composition of a biological sample is disclosed. A stimulated Raman scattering (SRS) image of the biological sample is received. The effect of light scattering in the received SRS image is computationally removed. An absolute concentration of total protein, total lipid, and/or water from the biological sample is determined.

20 Claims, 25 Drawing Sheets

(56) References Cited

U.S. PATENT DOCUMENTS

| | | |
|---|---|---|
| 2015/0185207 A1 | 7/2015 | Black et al. |
| 2016/0178439 A1 | 6/2016 | Freudiger et al. |
| 2016/0243261 A1* | 8/2016 | Min .................. A61K 49/0013 |

OTHER PUBLICATIONS

Kafri, R. et al. Dynamics extracted from fixed cells reveal feedback linking cell growth to cell cycle. Nature 494, 480-3 (2013) (4 pages).

Tzur, A., Kafri, R., LeBleu, V. S., Lahav, G. & Kirschner, M. W. Cell growth and size homeostasis in proliferating animal cells. Science 325, 167-71 (2009) (6 pages).

Son, S. et al. Direct observation of mammalian cell growth and size regulation. Nat. Methods 9, 910 (2012) (5 pages).

Popescu, G. et al. Optical imaging of cell mass and growth dynamics. Am. J. Physiol. Physiol. 295, C538-C544 (2008) (7 pages).

Cooper, K. L. et al. Multiple phases of chondrocyte enlargement underlie differences in skeletal proportions. Nature 495, 375 (2013) (5 pages).

Cadart, C. et al. Size control in mammalian cells involves modulation of both growth rate and cell cycle duration. Nat. Commun. 9, 3275 (2018) (16 pages).

Freudiger, C. W. et al. Label-free biomedical imaging with high sensitivity by stimulated Raman scattering microscopy. Science (80-.). 322, 1857-1861 (2008) (6 pages).

Wei, M. et al. Volumetric chemical imaging by clearing-enhanced stimulated Raman scattering microscopy. Proc. Natl. Acad. Sci. 201813044 (2019) (10 pages).

Fu, D., Holtom, G., Freudiger, C., Zhang, X. & Xie, X. S. Hyperspectral imaging with stimulated Raman scattering by chirped femtosecond lasers. J. Phys. Chem. B 117, 4634-4640 (2013) (7 pages).

Fu, D. et al. Quantitative chemical imaging with multiplex stimulated Raman scattering microscopy. J. Am. Chem. Soc. 134, 3623-3626 (2012) (4 pages).

Lu, F.-K. et al. Multicolor stimulated Raman scattering microscopy. Mol. Phys. 110, 1927-1932 (2012) (9 pages).

Shin, S. et al. Optical diffraction tomography using a digital micromirror device for stable measurements of 4D refractive index tomography of cells. in Quantitative Phase Imaging II 9718, 971814 (2016) (9 pages).

Cheng, J.-X. & Xie, X. S. Vibrational spectroscopic imaging of living systems: An emerging platform for biology and medicine. Science (80-.). 350, aaa8870 (2015) (11 pages).

Ji, M. et al. Label-free imaging of amyloid plaques in Alzheimer's disease with stimulated Raman scattering microscopy. Sci. Adv. 4, eaat7715 (2018) (9 pages).

Alberts B, Johnson A, Lewis J, et al. The Chemical Components of a Cell. in Molecular Biology of the Cell. 4th edition. (Garland Science, 2002) (21 pages).

Lu, F.-K. et al. Label-free DNA imaging in vivo with stimulated Raman scattering microscopy. Proc. Natl. Acad. Sci. 112, 11624-11629 (2015) (7 pages).

King, J. L. & Jukes, T. H. Non-Darwinian evolution. Science (80-.). 164, 788-98 (1969) (11 pages).

Jacques, S. L. Optical properties of biological tissues: a review. Phys. Med. Biol. 58, R37 (2013) (29 pages).

Min, W., Freudiger, C. W., Lu, S. & Xie, X. S. Coherent Nonlinear Optical Imaging: Beyond Fluorescence Microscopy. Annu. Rev. Phys. Chem (2011). doi:10.1146/annurev.physchem.012809. 103512 (27 pages).

Orringer, D. A. et al. Rapid intraoperative histology of unprocessed surgical specimens via fibre-laser-based stimulated Raman scattering microscopy. Nat. Biomed. Eng. 1, 27 (2017) (14 pages).

Sarri, B. et al. Fast stimulated Raman imaging for intraoperative gastro-intestinal cancer detection. arXiv Prepr. arXiv1902.08859 (2019) (11 pages).

International Search Report and Written Opinion of International Searching Authority for Application No. PCT/US2020/031943, dated Aug. 7, 2020 (8 pages).

\* cited by examiner

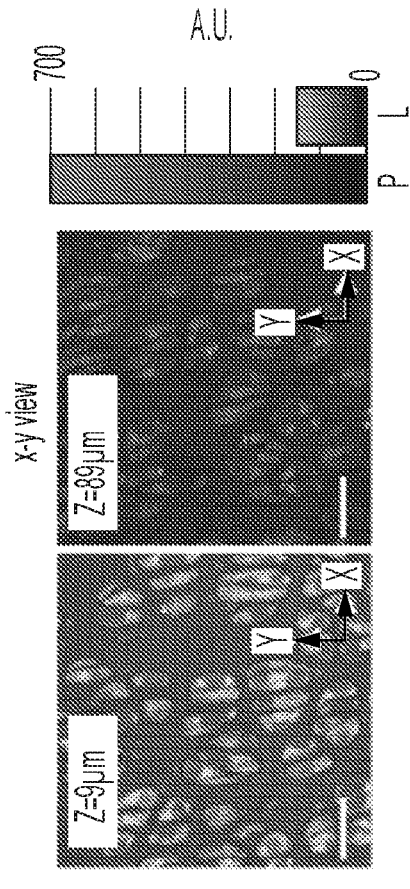
FIG. 14A
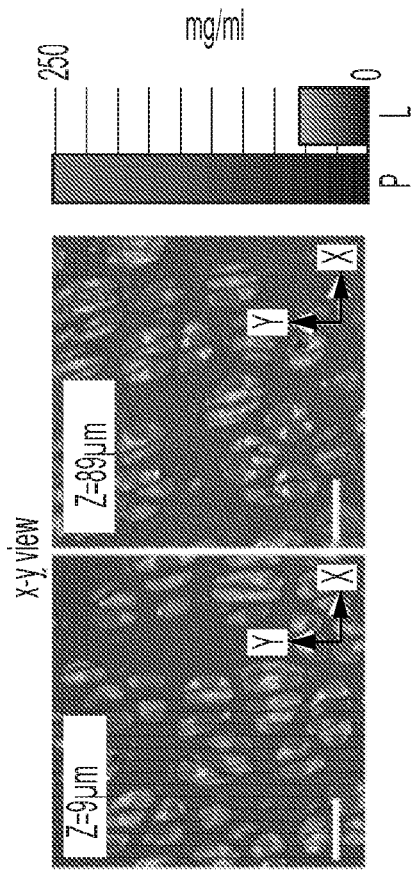
FIG. 14B
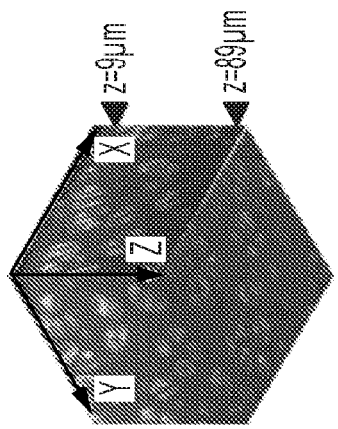
Spectral decomposition
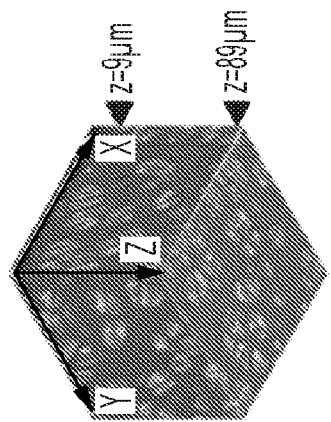
Absolute concentration

IN SITU MEASUREMENT OF ABSOLUTE CONCENTRATIONS BY NORMALIZED RAMAN IMAGING

CROSS-REFERENCE TO RELATED APPLICATIONS

This application is the National Phase of International Application PCT/US2020/031943, filed on May 7, 2020, which designated the United States, which claims priority to and the benefit of U.S. Provisional Patent Application No. 62/844,320, filed on May 7, 2019, each of which is hereby incorporated by reference herein in its entirety.

GOVERNMENT SUPPORT

This invention was made with government support under Grant No. R01 GM026875 awarded by National Institutes of Health. The government has certain rights in the invention.

TECHNICAL FIELD

This disclosure relates generally to Raman imaging, and more particularly, to systems and methods for normalizing Raman imaging.

BACKGROUND

Accurate measurement of mass and chemical composition at single cell resolution is critical for understanding cell physiology (including size regulation, growth, differentiation, and homeostasis) at the cell, tissue, and organism level, as well as, in the context of disease and degeneration. Conventional methods developed to measure single cell mass or volume includes the use of fluorescence reporters, Coulter counter, Suspended Microchannel Resonator (SMR), Quantitative Phase Microscopy (QPM), and Fluorescence eXclusion Microscopy (FXM). However, these methods generally require cell suspension or 2D cell culture. Consequently, anatomical and tissue-context information is lost. Moreover, these methods do not distinguish between the mass contributions of proteins, lipids, and other materials. The present disclosure is directed to solving these problems and addressing other needs.

SUMMARY

According to some implementations of the present disclosure, a method for measuring a composition of a biological sample is disclosed. A stimulated Raman scattering (SRS) image of the biological sample is received. The effect of light scattering in the received SRS image is computationally removed. An absolute concentration of total protein, total lipid, and/or water from the biological sample is determined.

In some implementations, the SRS image is received from a stimulated Raman scattering (SRS) microscopy.

In some implementations, based at least in part on the determined absolute concentration of the total protein, the total lipid, and/or the water from the biological sample, a protein mass and/or a lipid mass of the biological sample is assessed. In some such implementations, the protein mass and/or the lipid mass of the biological sample is assessed in situ.

In some implementations, SRS images are acquired at selected Raman bands. An SRS intensity of each of the selected Raman bands is determined. The determined SRS intensity of the each of the selected Raman bands is mapped to a corresponding protein, lipid, or water fraction. In some such implementations, background subtraction and/or flat field correction is applied to the acquired SRS images.

In some implementations, the selected Raman bands include a CH3 Raman band, a CH2 Raman band, an H2O Raman band, or any combination thereof. In some implementations, the Raman bands are selected from high-wavenumber region and/or fingerprint region.

In some implementations, the mapping is accomplished through spectral decomposition. In some implementations, the spectral decomposition includes three or more spectral components.

In some implementations, a decomposition matrix is determined from SRS intensity and concentration of calibration standard samples. Spectral decomposition is processed by matrix multiplication of the determined decomposition matrix with the acquired SRS images. In some implementations, the decomposition matrix is determined by measuring the SRS intensity at CH3, CH2, and/or H2O bands of the calibration standard samples.

In some implementations, the calibration standard samples include a protein solution, a lipid solution, water, or any combination thereof. In some implementations, the protein solution includes bovine serum albumin (BSA). In some implementations, the lipid solution includes dioleoylphosphocholine (DOPC).

In some implementations, the calibration standard samples are assembled into a single sample holder and imaged at a maximum intensity z position.

In some implementations, output of the processing the spectral decomposition is proportional to a concentration of a respective chemical component. In some implementations, output of the processing the spectral decomposition is proportional to an attenuation due to light scattering. In some implementations, the stimulated Raman scattering (SRS) image is received from an optical system; and the attenuation due to light scattering and/or imperfection of the optical system is spatially heterogeneous.

In some implementations, the computationally removing the effect of light scattering in the received SRS image includes determining an attenuation to output a normalization mask; and the determining the absolute concentration of the total protein, the total lipid, and/or the water from the biological sample includes dividing the processed spectral decomposition with the normalization mask. In some such implementations, the normalization mask is determined from a pixel-by-pixel sum of the spectral decomposition.

In some implementations, mass concentration of protein or lipid in the biological sample is estimated by multiplying the absolute concentration of the total protein or the total lipid with mass density of pure protein or pure lipid. In some implementations, the mass density of pure protein is about 1.364 g/ml; and wherein the mass density of pure lipid is about 1.0101 g/ml.

According to some implementations of the present disclosure, a system includes a control system and a memory. The control system includes one or more processors. The memory has machine readable instructions stored thereon. The control system is coupled to the memory, and any of the methods disclosed above is implemented when the machine executable instructions in the memory are executed by at least one of the one or more processors of the control system.

According to some implementations of the present disclosure, a system for measuring a composition of a biological sample includes a control system configured to implement any of the methods disclosed above.

According to some implementations of the present disclosure, a computer program product includes instructions which, when executed by a computer, cause the computer to carry out any of the methods disclosed above. In some implementations, the computer program product is a non-transitory computer readable medium.

The foregoing and additional aspects and implementations of the present disclosure will be apparent to those of ordinary skill in the art in view of the detailed description of various embodiments and/or implementations, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

FIG. 14A illustrates the spectral decomposition showing a decrease of signal with imaging depth, according to some implementations of the present disclosure;

FIG. 14B illustrates the NoRI image of protein and lipid mass density from FIG. 14A after light scattering normalization, according to some implementations of the present disclosure;

Figure 1:
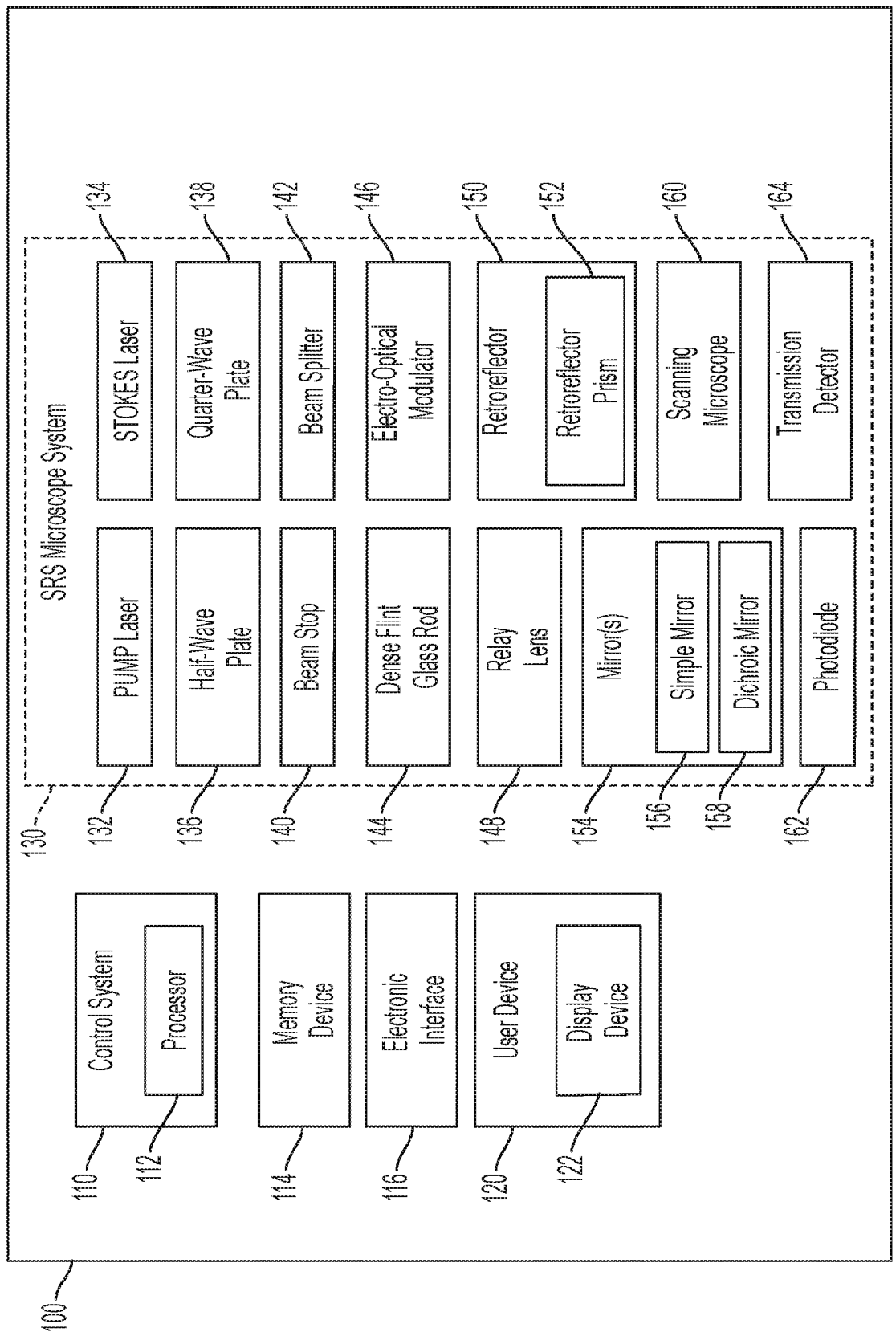
FIG. 1 is a functional block diagram of a system, according to some implementations of the present disclosure.

While the present disclosure is While the present disclosure is susceptible to various modifications and alternative forms, specific implementations have been shown by way of example in the drawings and will be described in further detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

The present disclosure is described with reference to the attached figures, where like reference numerals are used throughout the figures to designate similar or equivalent elements. The figures are not drawn to scale, and are provided merely to illustrate the instant disclosure. Several aspects of the disclosure are described below with reference to example applications for illustration.

Introduction

Accurate measurement of size and chemical composition at single cell resolution is critical for understanding cell physiology (including size regulation, growth, differentiation, and homeostasis) at the cell, tissue, and organism level, as well as, in the context of disease and degeneration. Conventional methods generally require cell suspension or 2D cell culture. Consequently, anatomical and tissue-context information is lost. Moreover, these methods do not distinguish between the mass contributions of proteins, lipids, and other materials.

Stimulated Raman scattering (SRS) microscopy can measure Raman signals of proteins and lipids in thick tissue specimens without any use of staining. SRS intensity is linearly proportional to the concentration of target chemical structures, which enables many quantitative applications. However, in tissue samples, SRS intensity is not fully quantitative due to the irregular light scattering caused by the sample. This problem can be partially overcome by slicing the tissue into thin sections and/or by reducing the tissue light scattering by optical clearing.

Nonetheless, the three-dimensional information is lost with thin sectioning, and conventional optical clearing is incompatible for imaging lipids. To overcome these limitations, according to some implementations of the present disclosure, the effect of light scattering in thick biological samples is instead computationally removed by directly measuring the attenuation due to light scattering. Thus, the present disclosure provides a powerful and versatile new method for assessing protein and lipid mass in situ.

According to some implementations of the present disclosure, Normalized Raman Imaging (NoRI), a Stimulated Raman Scattering (SRS) microscopy method is introduced, which computationally removes the effect of tissue light scattering. First, NoRI provides high resolution measurements of the absolute concentration of total protein, total lipid, and water from live and/or fixed thick tissue samples with single cell resolution. Second, NoRI can also be applied to other Raman bands. Third, NoRI enables study of the protein, lipid, and water concentration variation associated with development and diseases.

The NoRI System Overview

Referring to FIG. 1, a system 100, according to some implementations of the present disclosure, is illustrated. The system 100 includes a control system 110, a memory device 114, an electronic interface 116, one or more user devices 120 or external devices, and an SRS microscope system 130.

The control system 110 includes one or more processors 112 (hereinafter, processor 112). The control system 110 is generally used to control (e.g., actuate) the various components of the system 100 and/or analyze data obtained and/or generated by the components of the system 100. The processor 112 can be a general or special purpose processor or microprocessor. While one processor 112 is shown in FIG. 1, the control system 110 can include any suitable number of processors (e.g., one processor, two processors, five processors, ten processors, etc.) that can be in a single housing, or located remotely from each other. The control system 110 can be coupled to and/or positioned within, for example, a housing of the user device 120, and/or within a housing of one or more components of the SRS microscope system 130. The control system 110 can be centralized (within one such housing) or decentralized (within two or more of such housings, which are physically distinct). In such implementations including two or more housings containing the control system 110, such housings can be located proximately and/or remotely from each other.

The memory device 114 stores machine-readable instructions that are executable by the processor 112 of the control system 110. The memory device 114 can be any suitable computer readable storage device or media, such as, for example, a random or serial access memory device, a hard drive, a solid state drive, a flash memory device, etc. While one memory device 114 is shown in FIG. 1, the system 100 can include any suitable number of memory devices 114 (e.g., one memory device, two memory devices, five memory devices, ten memory devices, etc.). The memory device 114 can be coupled to and/or positioned within a housing of the user device 120, and/or within a housing of one or more components of the SRS microscope system 130. Like the control system 110, the memory device 114 can be centralized (within one such housing) or decentralized (within two or more of such housings, which are physically distinct).

The electronic interface 116 is configured to receive data (e.g., SRS intensity data, SRS image data) from the SRS microscope system 130 such that the data can be stored in the memory device 114 and/or analyzed by the processor 112 of the control system 110. For example, magnitude and phase (e.g., equivalently in-phase and quadrature components) of the pump (or Stokes in the alternative configuration) light intensity is obtained at the photo detector. These quantities can be obtained at the desired Raman bands (CH3 band, CH2 band, H2O band, or any desired band) for signal. In addition, in some implementations, quantities can be obtained at the off-peak and without signal to measure the background level. Especially, the background measured with closed shutter is used to subtract the background level from sample data. This background subtraction is further disclosed, for example, in Image Processing of SRS Intensity Images section of the present disclosure.

Additionally, in some implementations, the following information of the system 100 can be electronically monitored and/or maintained at a tight range by internal feedback and/or by the design of the subcomponents of the system 100, with some of these variables recorded along with the SRS image data: the position of delay motors, the position of the intensity attenuator motors, the state of the laser (wavelength, shutter, status), the bias voltage of the photo detector, driving voltage of the EOM, the temperature and the DC power of RF amplifier for EOM driver, or any combination thereof.

In some implementations, the system 100 can include (i) a lock-in amplifier, (ii) a band pass filter, (iii) an analog-to-digital converter, or (iv) any combination thereof. In some such implementations, these components may be considered a part of the electronic interface 116 and/or of the microscope 130.

Further, in some implementations, the electronic interface 116 can communicate with the SRS microscope system 130 using a wired connection or a wireless connection (e.g., using an RF communication protocol, a WiFi communication protocol, a Bluetooth communication protocol, over a cellular network, etc.). The electronic interface 116 can include an antenna, a receiver (e.g., an RF receiver), a transmitter (e.g., an RF transmitter), a transceiver, or any combination thereof. The electronic interface 116 can also include one more processors and/or one more memory devices that are the same as, or similar to, the processor 112 and the memory device 114 described herein. In some implementations, the electronic interface 116 is coupled to or integrated in the user device 120. In some other implementations, the electronic interface 116 is coupled to or integrated (e.g., in a housing) with the control system 110 and/or the memory device 114.

The user device 120 includes a display device 122. The user device 120 can be, for example, a mobile device such as a smart phone, a tablet, a laptop, a desk monitor, a hospital or lab display, or the like. Alternatively, the user device 120 can be an external sensing system, a television (e.g., a smart television) or another smart home device (e.g., a smart speaker(s) such as Google Home, Amazon Echo, Alexa etc.). In some implementations, the user device is a wearable device (e.g., a smart watch). The display device 122 is generally used to display image(s) including still images, video images, or both. In some implementations, the display device 122 acts as a human-machine interface (HMI) that includes a graphic user interface (GUI) configured to display the image(s) and an input interface. The display device 122 can be an LED display, an OLED display, an LCD display, or the like. The input interface can be, for example, a touchscreen or touch-sensitive substrate, a mouse, a keyboard, or any sensor system configured to sense inputs made by a human user interacting with the user device 120. In some implementations, one or more user devices can be used by and/or included in the system 100.

Still referring to FIG. 1, in some implementations, the SRS microscope system 130 can include a tunable femtosecond laser 132, a fixed wavelength femtosecond pulse laser 134, one or more first half wave plates 136, one or more quarter wave plates 138, one or more beam stops 140, one or more beam splitters 142, one or more dense flint glass rods 144, one or more electro-optical modulators 146, one or more relay lenses 148, one or more retroreflectors 150, one or more mirrors 154, a scanning microscope 160, and a photodiode 162. In some implementations, the one or more retroreflectors 150 include a retroreflector prism 152. In some implementations, the one or more mirrors 154 include a simple mirror 156, a dichroic mirror 158, or both. In some implementations, the SRS microscope system 130 further includes a transmission detector 164.

In some implementations, the SRS microscope system 130 can include a signal processing unit (e.g., a signal processor or any signal processing component). The signal processing unit receives the output of a detector (e.g., the transmission detector 164 or an epi-directional detector), processes the raw signal from the detector, extracts relevant electrical signal from the raw signal, and converts the signal to a digital form that can be further processed and stored via the control system.

While the control system 110 and the memory device 114 are described and shown in FIG. 1 as being a separate and distinct component of the system 100, in some implementations, the control system 110 and/or the memory device 114 are integrated in the user device 120 and/or one or more components of the SRS microscope system 130. Alternatively, or additionally, in some implementations, the control system 110 or a portion thereof (e.g., the processor 112) can be located in a cloud (e.g., integrated in a server, integrated in an Internet of Things (IoT) device, connected to the cloud, be subject to edge cloud processing, etc.), located in one or more servers (e.g., remote servers, local servers, etc.), or any combination thereof.

Further, while the SRS microscope system 130 is illustrated in FIG. 1 as including the various components described above, a SRS microscope system for implementing NoRI can include more or fewer components in the same or alternative arrangements. For example, a first alternative SRS microscope system (e.g., a femtosecond laser SRS microscope system) can include an epi-directional detector instead of a transmission detector (e.g., the transmission detector 164 of the SRS microscope system 130 in FIG. 1).

As another example, a second alternative SRS microscope system (e.g., a picosecond laser SRS microscope system) can include a tunable picosecond laser (e.g., replacing the tunable femtosecond laser 132), a fixed wavelength picosecond pulse laser (e.g., replacing the fixed wavelength femtosecond pulse laser 134), one or more first half wave plates 136, one or more quarter wave plates 138, one or more beam stops 140, one or more beam splitters 142, one or more electro-optical modulators 146, one or more mirrors 154, the scanning microscope 160, the photodiode 162, a signal processor, or any combination thereof. In some such implementations, the signal processor can include (i) a lock-in amplifier, (ii) a band pass filter, (iii) an analog-to-digital converter, or (iv) any combination thereof.

In some implementations, the systems and methods disclosed herein for measuring a composition of a tissue sample and/or for computationally removing the effect of light scattering can work with any SRS microscope. Additional examples of such SRS microscope are illustrated and described with reference to FIGS. 2A-2D.

Stimulated Raman Scattering Microscope

Absolute quantification requires a highly stable SRS microscope that can measure SRS intensity with excellent repeatability. One key innovation of the disclosed NoRI algorithm (and its related systems and methods) is that a physical quantity with absolute unit (mg/ml) can be computed from the raw data in an arbitrary unit (A.U.). The NoRI algorithm's capability to obtain a physical unit measurement from an arbitrary unit measurement does not depend on the stability. In some implementations, the system stability only affects the figure of merit. As an example, when NoRI normalization is applied to data from a less stable SRS microscope, we get a worse figure of merit. But the result is still an absolute concentration in a physical unit (mg/ml) albeit with a larger error range.

The SRS microscope systems disclosed herein can provide superb stability and improve the accuracy of the disclosed NoRI algorithm, resulting in about 15 mg/ml accuracy. Additionally, the stability can be achieved by using additional methods (e.g., enclosure, environmental control including thermal regulation, improved optomechanics including short optical post, low thermal expansion mount) on any SRS microscope systems.

Thus, a custom SRS microscope (e.g., the SRS microscopes 130A in FIG. 2A, 130B in FIG. 2B, 130C in FIG. 2C, and 130D in FIG. 2D) can be built. One custom aspect of the microscope is in the improvement of the stability by using various high-stability elements including thermal isolation, short and large diameter posts, and the use of high stability optomechanics components. When NoRI algorithm is applied to SRS data generated from less stable SRS microscopes, the normalization still works, but the result has higher noise (e.g., can be less accurate).

For example, the custom SRS microscope can include a tunable femtosecond pulse laser and a dense flint dispersion element for spectral-focusing. In some implementations, the design of the SRS microscope is primarily determined for the reproducibility of SRS intensity between repeated retuning of the pump beam wavelength, and full automation of acquisition of the three Raman bands.

Figure 2A:
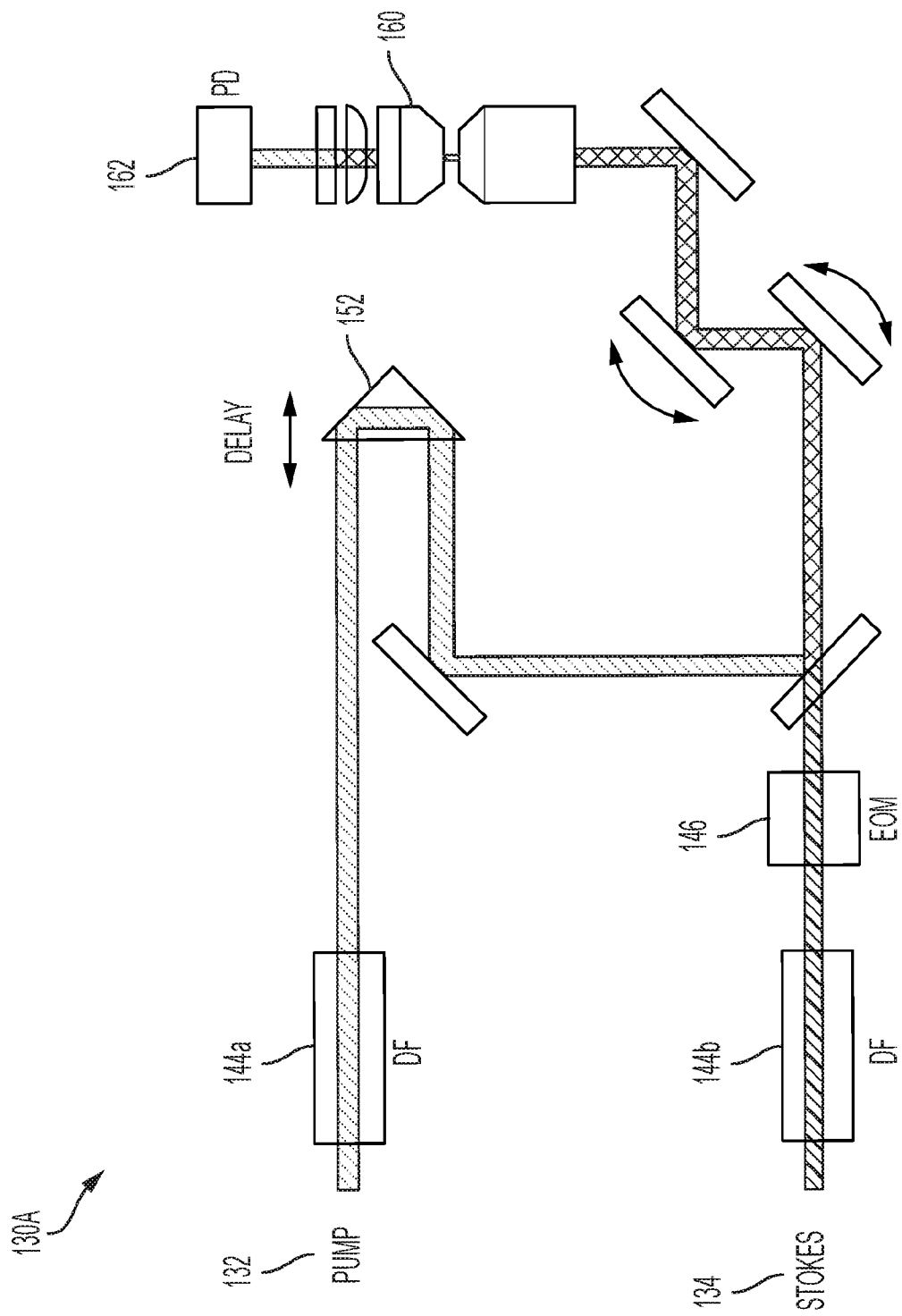
FIG. 2A illustrates a schematic diagram of an example femtosecond SRS microscope system, according to some implementations of the present disclosure.

Referring to FIG. 2A, a schematic diagram of an example femtosecond SRS microscope system 130A is illustrated, according to some implementations of the present disclosure. The SRS microscope system 130A is the same as, or similar to, the SRS microscope system 130 of the system 100 (FIG. 1), where identical reference numbers are used for identical elements. The SRS microscope system 130A includes a tunable femtosecond laser 132 (PUMP), a fixed wavelength femtosecond pulse laser 134 (STOKES), two dense flint glass rods 144a and 144b (DF), an electro-optical modulator 146 (EOM), a motorized retroreflector prism 152 (DELAY), and a photodiode 162 (PD). The SRS signal is detected by a transmission detector 164 (FIG. 1). In some implementations, the photodiode 162 is the transmission detector. Images are acquired by point scanning at the sample, via, for example, a scanning microscope 160.

Figure 2B:
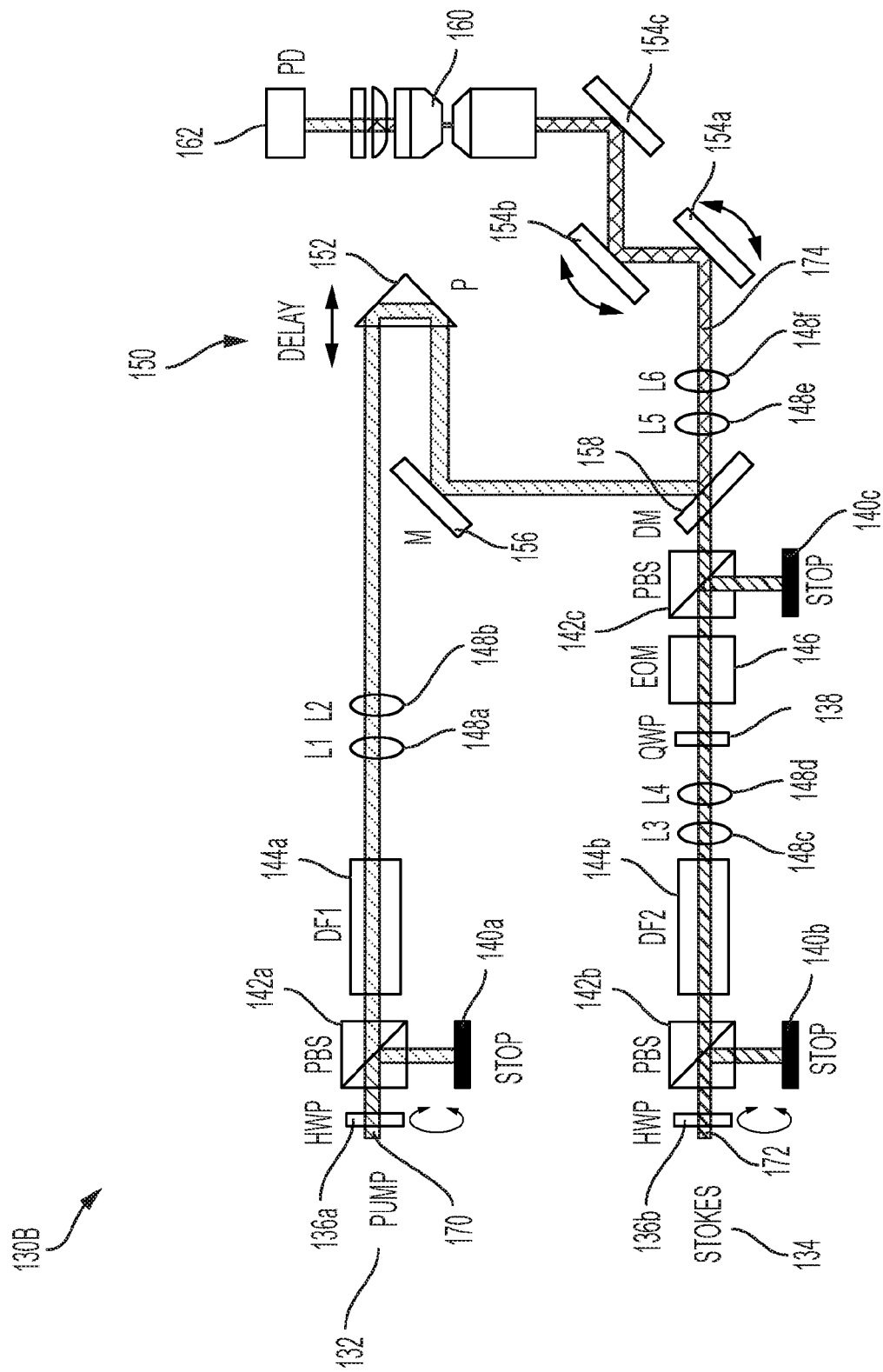
FIG. 2B illustrates a schematic diagram of an example femtosecond SRS microscope system, according to some implementations of the present disclosure.

Referring to FIG. 2B, a schematic diagram of an example femtosecond SRS microscope system 130B is illustrated, according to some implementations of the present disclosure. The SRS microscope system 130B is the same as, or similar to, the SRS microscope system 130 of the system 100 (FIG. 1) and/or the SRS microscope system 130A (FIG. 2), where identical reference numbers are used for identical elements. The light source includes a tunable femtosecond laser 132 (PUMP), such as a dual-output tunable femtosecond laser (e.g., Spectra-Physics, Insight X3), which provides a tunable beam 170 (e.g., at a range of 680-1040 nm). In some implementations, the SRS microscope system 130B also includes a fixed wavelength femtosecond pulse laser 134 (STOKES), which provides a fixed wavelength beam 172 (e.g., at 1045 nm). The tunable beam 170 and the fixed wavelength beam 172 are used as pump beam and Stokes beam, respectively.

In some implementations, the laser power is reduced by a pair of attenuators consisting of motor controlled half wave plates and cube polarizers. For example, as shown, the laser power from the tunable femtosecond laser 132 is reduced by a first half wave plate 136a (HWP) and a first polarizing beam splitter 142a (PBS). A portion of the split beam 170 from the tunable femtosecond laser 132 is directed to a first beam stop 140a (STOP).

The pump beam power sample was about 52-60 mW. The beam height from the optical table was reduced by using periscope to increase the long term stability of the optomechanics. The pump beam is chirped by passing through a first glass rod 144a (DF1), such as a high dispersion dense flint glass rod (e.g., Casix, SF57). The pump beam then passes through relay lenses 148a (L1) and 148b (L2) for adjusting the beam diameter. A motor-controlled retroreflector 150 (DELAY) controls the optical path length of the pump beam, after the beam diameter is adjusted. For example, the motor-controlled retroreflector 150 (DELAY) includes a retroreflector prism 152 (P).

In some implementations, as shown, the laser power from the fixed wavelength femtosecond pulse laser 134 is reduced by a second half wave plate 136b (HWP) and a second polarizing beam splitter 142b (PBS). A portion of the split beam 172 from the fixed wavelength femtosecond pulse laser 134 is directed to a second beam stop 140b (STOP). The Stokes beam power at the sample was about 25 mW. The beam height from the optical table was reduced by using periscope to increase the long term stability of the optomechanics. The Stokes beam is chirped by passing through a second glass rod 144b (DF2), such as a high dispersion dense flint glass rod (e.g., Casix, SF57).

The pump beam then passes through relay lenses 148c (L3) and 148d (L4) for adjusting the beam diameter, and subsequently through a quarter wave plate 138 (QWP). Further, in some implementations, the Stokes beam intensity is then modulated by an electro-optical modulator 146 (EOM) (e.g., Thorlabs EO-AM-R-20-C2) at about 20 MHz. The modulated Stokes beam can be further reduced by a third polarizing beam splitter 142c (PBS), and another portion of the split beam 172 is directed to a third beam stop 140c (STOP). The remaining Stokes beam 172 is co-linearly combined with the remaining pump beam 170 using dichroic mirror 158 (DM) and mirror 156 (M). In some implementations, the combined beam 174 passes through relay lenses 148e (L5) and 148f (L6) for adjusting the beam diameter.

The combined beam 174 is then directed (via, for example, mirrors 154a, 154b, and 154c) to a scanning microscope 160 to image the sample by point scanning. The stimulated Raman loss of the pump beam is measured by a photodiode 162 (PD) on the trans-side of the sample. In some implementations, the photodiode 162 includes a high speed photodiode (e.g., Thorlabs, FDS1010).

The photo current is converted to voltage by a 50-ohm resister, filtered by a 3-30 MHz band pass filter, and amplified by a lock-in amplifier (e.g., Zurich Instruments, HF2LI) at the EOM modulation frequencies. The demodulation amplitude of the lock-in amplifier is mapped to images in real time by analog to digital data acquisition board (e.g., Olympus, Analog Box) synchronized to the scanning microscope (e.g., Olympus, FV3000).

As shown in FIGS. 2A-2B, the SRS microscope system 130A and/or the SRS microscope system 130B can determine the stimulated Raman loss measurement from the pump beam 170. In some implementations, it is also possible to flip the alignment of the pump beam 170 and the Stokes beam 172, and measure stimulated Raman gain from the Stokes beam 172 instead.

Figure 2C:
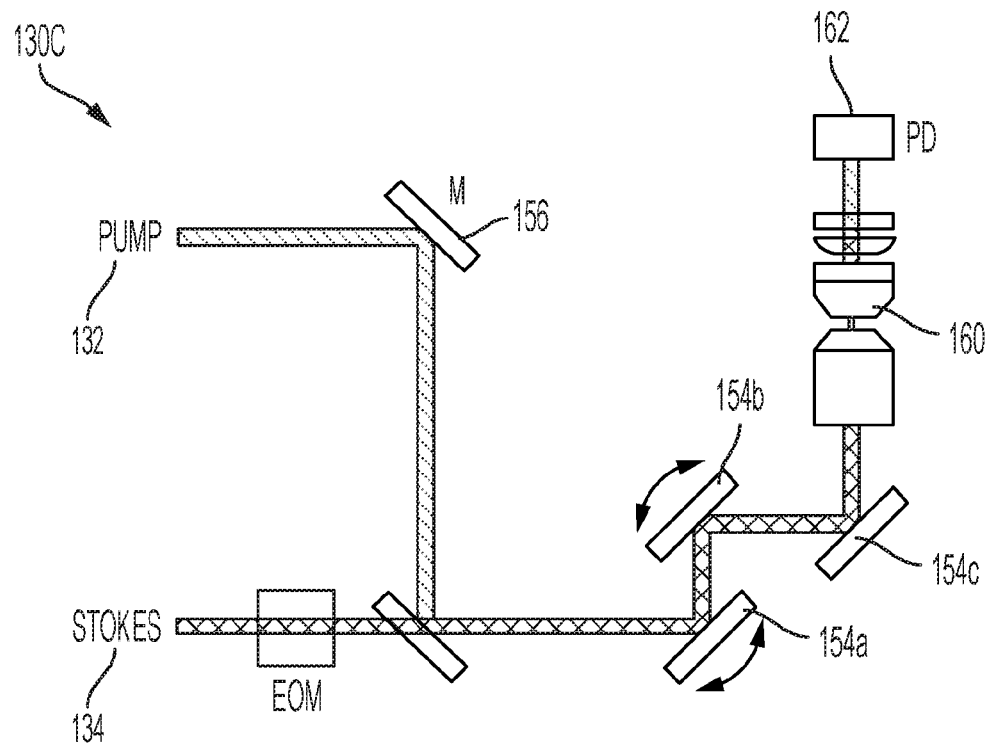
FIG. 2C illustrates a schematic diagram of an example picosecond SRS microscope system, according to some implementations of the present disclosure.

Referring to FIG. 2C, a schematic diagram of an example picosecond SRS microscope system 130C is illustrated, according to some implementations of the present disclosure. The picosecond SRS microscope system 130C is the same as, or similar to, the femtosecond SRS microscope system 130A (FIG. 2A) and/or the femtosecond SRS microscope system 130B (FIG. 2B), where like reference numbers are used for like elements, except that (i) the tunable femtosecond laser of FIGS. 2A-2B is replaced with a tunable picosecond laser 132, and (ii) the fixed wavelength femtosecond pulse laser of FIGS. 2A-2B is replaced with a fixed wavelength picosecond pulse laser 134. In some implementations, the dense flint glass rods are optional or unnecessary in the picosecond SRS microscope system 130C. Additionally, or alternatively, the retroreflector (including the motorized retroreflector prism) is optional or unnecessary in the picosecond SRS microscope system 130C.

Figure 2D:
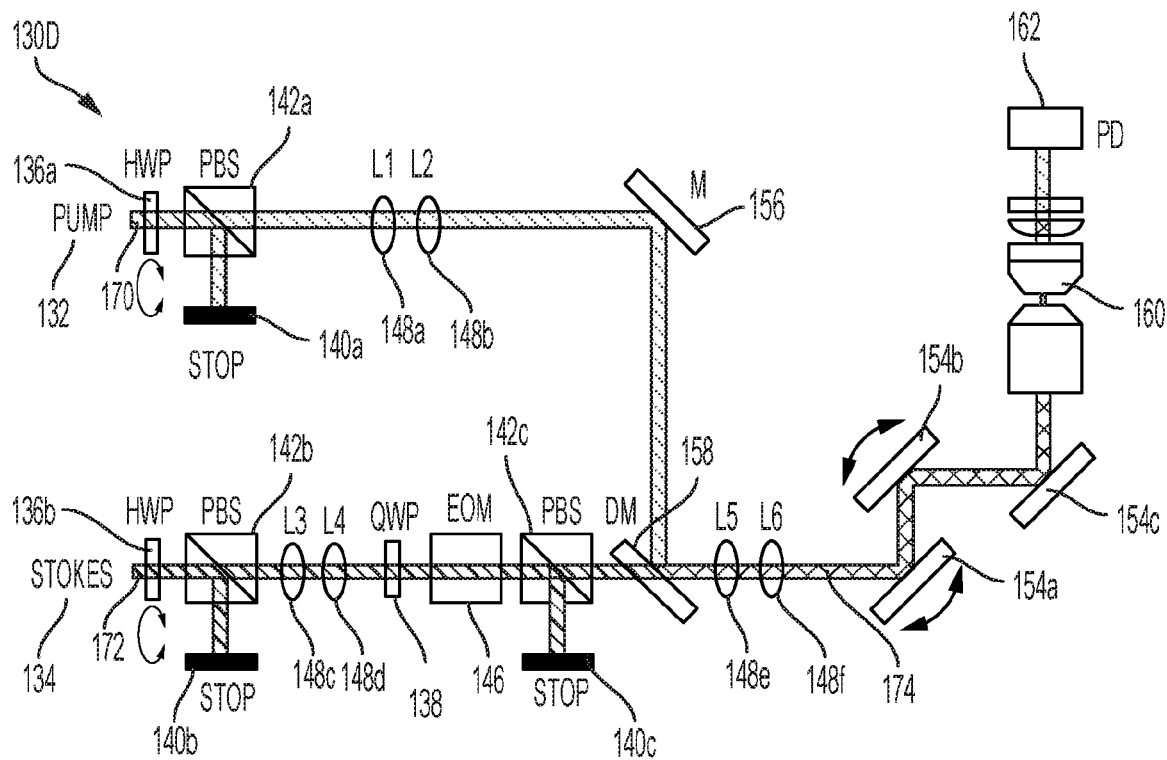
FIG. 2D illustrates a schematic diagram of an example picosecond SRS microscope system, according to some implementations of the present disclosure.

Referring to FIG. 2D, a schematic diagram of an example picosecond SRS microscope system 130D is illustrated, according to some implementations of the present disclosure. The picosecond SRS microscope system 130D is the same as, or similar to, the femtosecond SRS microscope system 130A (FIG. 2A), the femtosecond SRS microscope system 130B (FIG. 2B), and/or the picosecond SRS microscope system 130C (FIG. 3C), where like reference numbers are used for like elements. The picosecond SRS microscope system 130D includes a tunable picosecond laser 132 and a fixed wavelength picosecond pulse laser 134. In some implementations, the dense flint glass rods are optional or unnecessary in the picosecond SRS microscope system 130C. Additionally, or alternatively, the retroreflector (including the motorized retroreflector prism) is optional or unnecessary in the picosecond SRS microscope system 130C.

As shown in FIGS. 2C-2D, the SRS microscope system 130C and/or the SRS microscope system 130D can determine the stimulated Raman loss measurement from the pump beam 170. In some implementations, it is also possible to flip the alignment of the pump beam 170 and the Stokes beam 172, and measure stimulated Raman gain from the Stokes beam 172 instead.

Image Acquisition Settings

All SRS images are acquired with two microseconds per pixel dwell time. As such, a single 512×512 frame of SRS intensity image takes one second of acquisition time. In a typical NoRI acquisition, three Raman bands are acquired at $2853\ cm^{-1}$, $2935\ cm^{-1}$, and $3250\ cm^{-1}$. Raman band change requires wavelength change of tunable laser, which takes between about 7 to about 11 seconds to finish. When scanning large sample area, images was acquired at one Raman band for approximately 30 minutes, before imaging the same area in other Raman bands to avoid image misalignment problems.

The disclosed custom SRS microscope (e.g., the SRS microsystem 130 in FIG. 1, the SRS microsystem 130A in FIG. 2A, the SRS microsystem 130B in FIG. 2B) eliminates the need for optical adjustment (e.g., OPO tuning), and therefore significantly enhances the repeatability of SRS intensity measurements. Different Raman bands can be selected by tuning the wavelength of the pump beam 170 and/or the optical delay position (e.g., by adjusting the position of the retroreflector 150). When the pump beam center wavelength is fixed, spectral scanning can be acquired up to about $250\ cm^{-1}$ bandwidth, by scanning the motorized optical delay.

Figure 3:
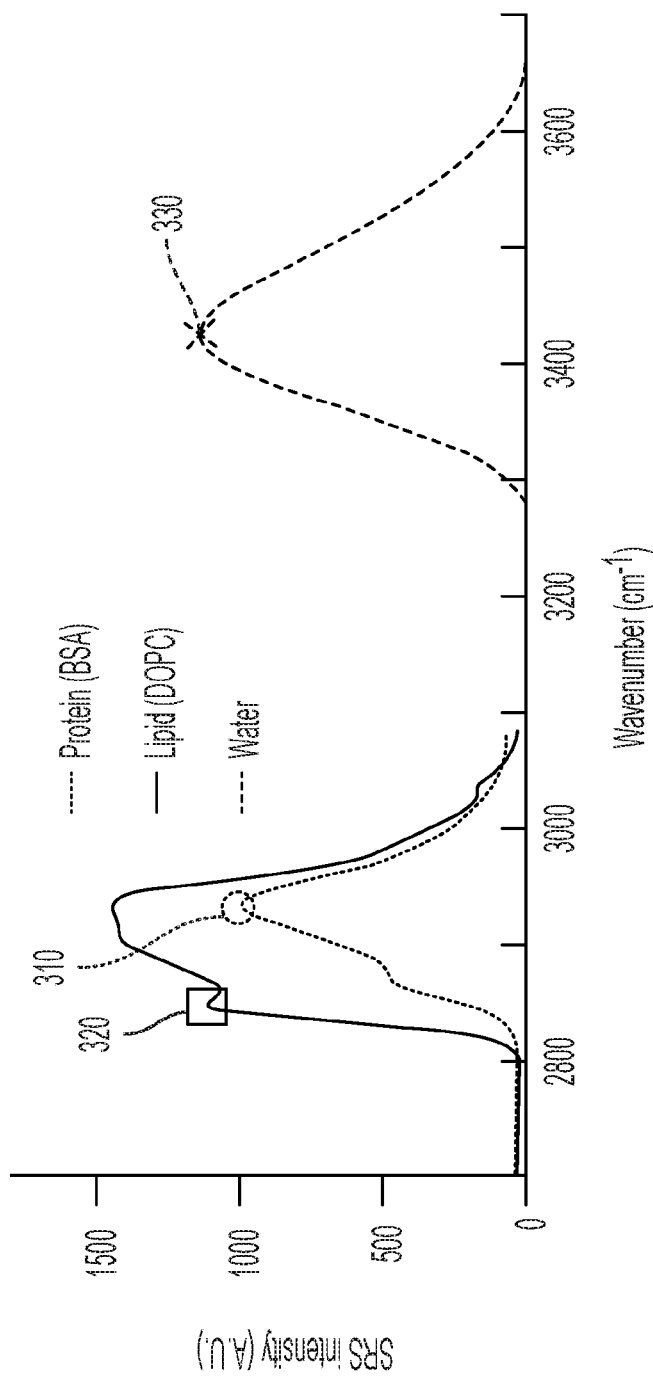
FIG. 3 illustrates the Raman spectrum of protein, lipid, and water acquired by scanning the motorized optical delay, according to some implementations of the present disclosure.

Referring to FIG. 3, the Raman spectrum of protein, lipid, and water is illustrated, according to some implementations of the present disclosure. The Raman spectrum was acquired by scanning the motorized optical delay at pump beam wavelengths of 800 nm for protein and lipid spectra, and at 770 nm for water spectrum. The circle 310, the square 320, and the blue cross 330 mark the position of $CH_3$ ($2935\ cm^{-1}$), $CH_2$ ($2853\ cm^{-1}$), and $H_2O$ ($3420\ cm^{-1}$) Raman bands, respectively. Raman bands at $2935\ cm^{-1}$ and $2853\ cm^{-1}$ show strong SRS signals originating from methyl groups and methylene groups, whereas water has a strong peak at $3420\ cm^{-1}$ from oxygen-hydrogen stretching modes. SRS images were acquired at these Raman bands, as referred as the $CH_3$ band, the $CH_2$ band, and the $H_2O$ band in the present disclosure. The SRS intensity of the $CH_3$, $CH_2$, and $H_2O$ Raman bands are mapped to protein, lipid, and water fractions through three-component spectral decomposition.

Calibration Standards

To establish spectral decomposition process for absolute quantification, the quantitative aspect of the SRS intensities of pure water and solution samples were examined. Bovine serum albumin (BSA) and dioleoyl-phosphocholine (DOPC) were selected as "calibration standard" for protein and lipid respectively. According to some implementations of the present disclosure, calibration standards include 30% BSA solution in water, 15 or 35% DOPC solution in 4-deuterated methanol, pure water and pure 4-deuterated methanol.

Figure 4:
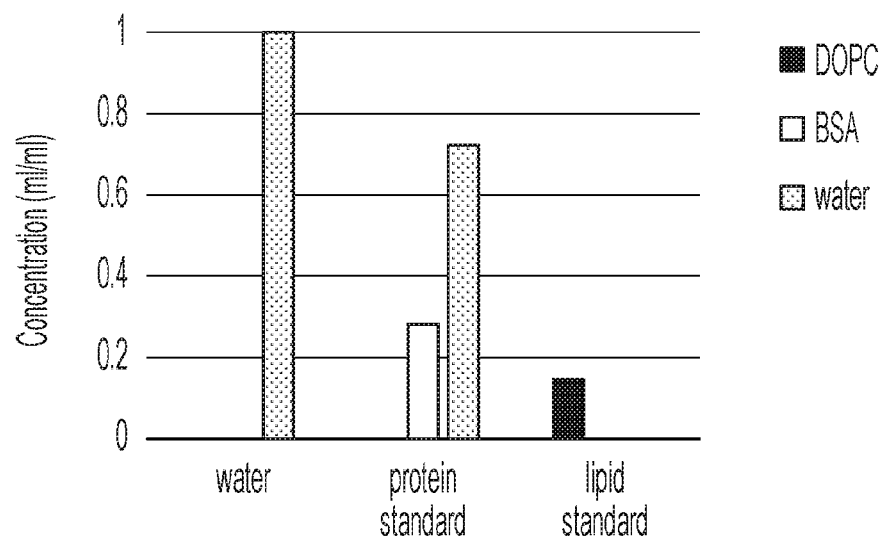
FIG. 4 illustrates the concentration of calibration standard samples, according to some implementations of the present disclosure.

All solution samples are mixed by measuring the weights of the components. BSA solution in water and DOPC solution in 4-deuterated methanol were mixed by weighing the components. For example, BSA powder (e.g., Sigma Aldrich, A7638) is weighed in a conical tube. Then, 150 mM, pH 7.6, phosphate buffer is added to make the concentration of 33% (w/w). The tube is tightly closed and placed in 40 degrees Celcius shaker until BSA is fully dissolved in buffer, while occasionally spinning down undissolved chucks that are stuck on the tube wall. DOPC powder is similarly weighted in a conical tube to which 4-deuterated methanol is added by weight. The final concentration in volume fraction is calculated from the mass fractions and the density of the pure components. The density of BSA is 1.364 g/ml and DOPC is 1.010 g/ml. The concentration of calibration standard samples is further illustrated in FIG. 4.

Measuring SRS Intensity Images of the Calibration Standards

Figure 5:
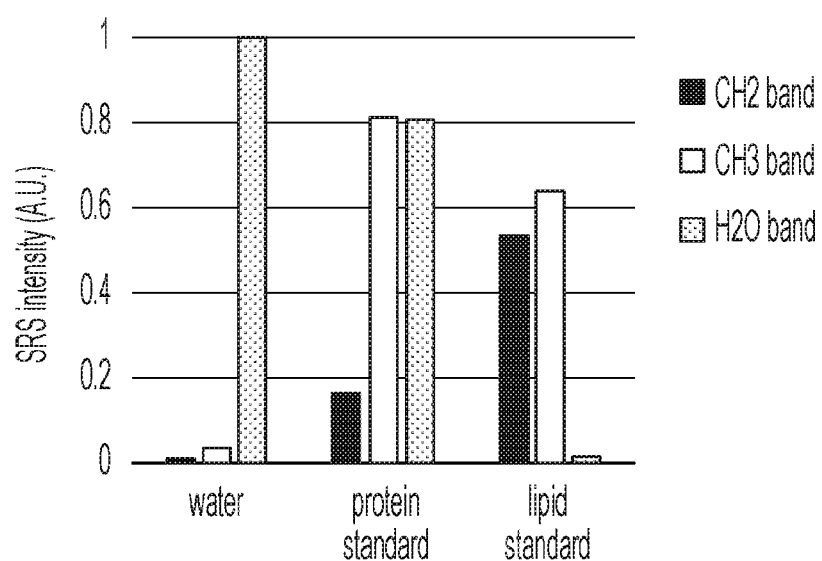
FIG. 5 illustrates the SRS intensity of calibration standards, according to some implementations of the present disclosure.

Sample holder was assembled on a glass slide by creating four (4) sample holding slots using double-sided tapes or adhesive sheets (e.g., Grace Biolabs, SA-S-1L). It was convenient to laser cut the adhesive sheets to have regular distance between the sample slots for automation of data acquisition. To prevent mixing of the adjacent samples, empty slots were placed between sample slots. The samples are injected to the holding slots by pipet. The sample volume is approximately 7 µl, with the thickness of 120 µm. A z stack of each sample with 2-5 µm step size was acquired. In order to capture the z plane of highest intensity immediately past the coverslip, the z stack started outside of the sample. The SRS intensity of calibration standards is further illustrated in FIG. 5.

Image Processing of SRS Intensity Images

To prepare SRS intensity images for the disclosed light scattering normalization algorithm, background subtraction and flat-field correction were applied. To ensure the linearity of the SRS intensity to concentration, dark noise is measured and subtracted from SRS images. Due to the aberration of optical system, the SRS intensity is 2D Gaussian function whose strongest intensity is in the center of the field of view. The spatial inhomogeneity is stable for a given wavelength over repeated retuning of the pump beam.

However, the position of the intensity centroid changes between different wavelengths of the tunable pump beam. The images of calibration standard samples capture this 2D intensity inhomogeneity. Flat-field correction mask was created from BSA sample images at CH3 and H2O Raman bands, and from the DOPC sample image at CH2 Raman band. The background level is subtracted from the images, then the intensity is normalized by dividing with the maximum intensity. Flat-field correction was applied by dividing sample images post-background subtraction with the intensity 2D mask of matching Raman band.

Example Methods and Algorithms

The following description of the flow diagram shown in FIG. 6 and the subsequent illustrative figures shown in FIGS. 7-13 is described in detail with reference to the components of the system 100 of FIG. 1.

Figure 6:
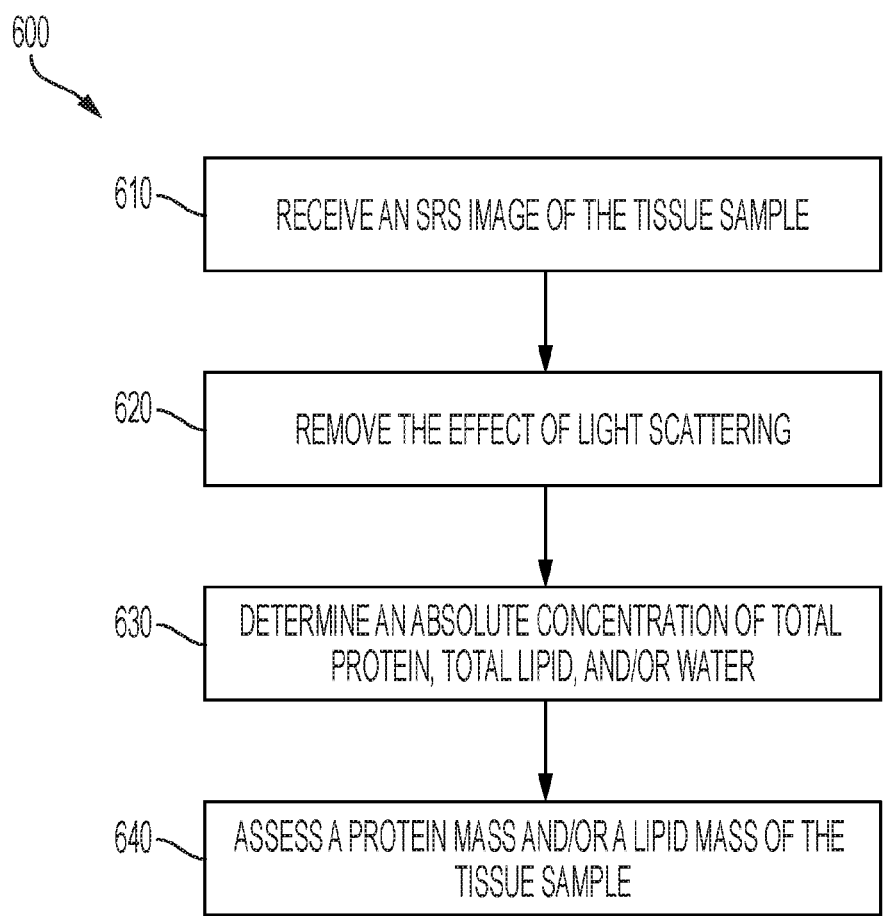
FIG. 6 is a flow diagram for a method of measuring a composition of a tissue sample, according to some implementations of the present disclosure.

According to some implementations of the present disclosure, FIG. 6 illustrations a flow diagram for a method 600 of measuring a composition of a biological sample (e.g., a cell sample, a tissue sample, a biological fluid sample, or the like). At step 610 of the method 600, a stimulated Raman scattering (SRS) image of the tissue sample is received. In some implementations, the SRS image is received from a stimulated Raman scattering (SRS) microscopy as described herein with respect to, for example, the SRS microscope system 130 (FIG. 1), the SRS microscope system 130A (FIG. 2A), and/or the SRS microscope system 130B (FIG. 2B).

At step 620 of the method 600, the effect of light scattering in the received SRS image is computationally removed. At step 630 of the method 600, an absolute concentration of total protein, total lipid, and/or water from the tissue sample is determined. In some implementations, the method 600 further includes the step 640, based at least in part on the determined absolute concentration of the total protein, the total lipid, and/or the water from the tissue sample, a protein mass and/or a lipid mass of the tissue sample is assessed. In some such implementations, the protein mass and/or the lipid mass of the tissue sample is assessed in situ.

Figure 7:
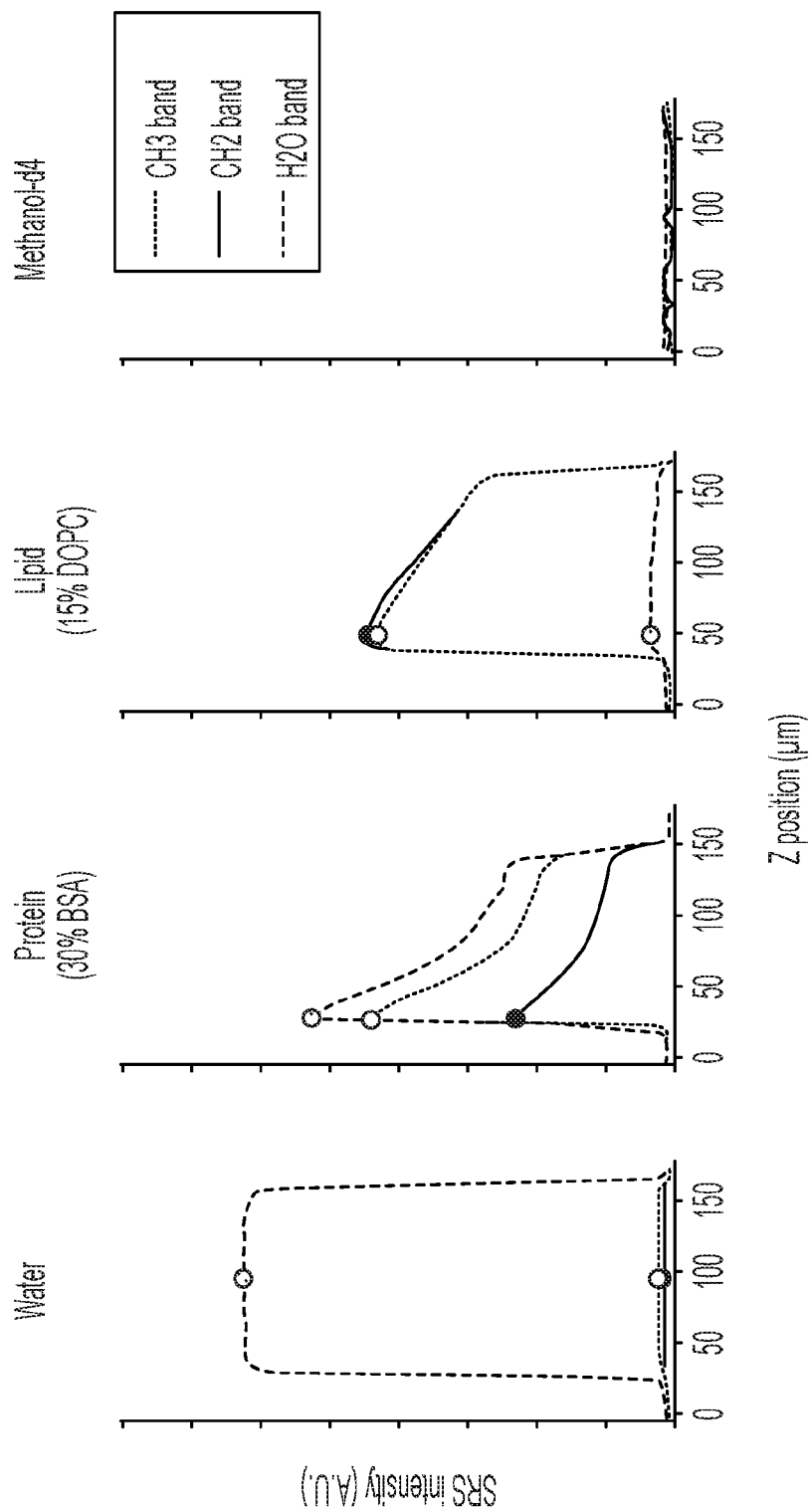
FIG. 7 illustrates the z-profiles of SRS intensity for water, protein calibration standard samples, lipid calibration standard samples, and deuterated methanol, according to some implementations of the present disclosure.

As disclosed herein, to establish spectral decomposition process for absolute quantification, the quantitative aspect of the SRS intensities of pure water and solution samples were examined. Spectral decomposition relies on the linear relation of the SRS signal intensity and the concentration of the measured molecule, which is constant in a solution sample. However, the signal intensity from a solution sample varies with the x, y, and z position of the image. The variation in x-y was corrected by flat field correction. However, the z-dependence was from the refractive index mismatch of the samples. For example, as shown in FIG. 7, the relationship between the z position and the SRS intensity is illustrated for water, protein calibration standard samples, lipid calibration standard samples, and deuterated methanol (e.g., solvent for lipid solution), according to some implementations of the present disclosure. The SRS intensity can be measured using a water-immersion objective lens. The circle marks show where the SRS signal intensity is taken for the calculation of decomposition matrix in FIG. 8.

When a water immersion objective lens is used, SRS intensity of water sample is independent of the z position, as the objective lens is perfectly corrected for water. But the intensity is the strongest at the surface immediately past the cover glass for BSA and DOPC samples, because the focus degrades as the light propagates further through the index-mismatched solutions. Therefore, all calibration standards are assembled into a single sample holder, and imaged at the maximum intensity z position where the optical aberration from the sample is minimal.

Figure 8:
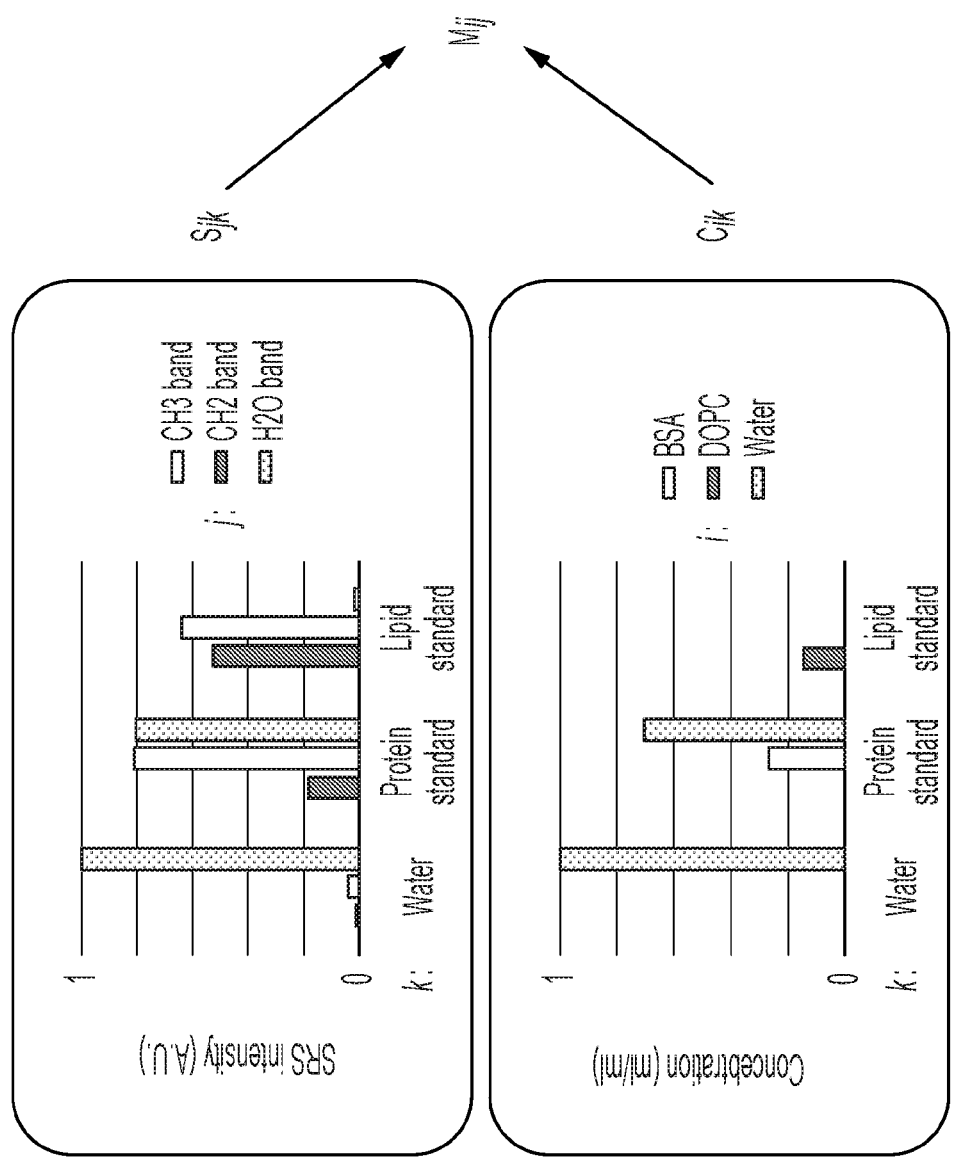
FIG. 8 illustrates the decomposition matrix calculated from SRS intensity and concentration of water, protein calibration standard samples, and lipid calibration standard samples, according to some implementations of the present disclosure.

By measuring the SRS intensity at the $CH_3$, $CH_2$, and $H_2O$ bands of the BSA, DOPC, and water calibration standards, decomposition matrix is solved by a simple matrix inversion:

$$M_{ij} = \Sigma_k C_{jk} S_{ik}^{-1} \quad \text{(Eq. 1)}$$

where $S_{ik}$ is the SRS signal at the i-th Raman band (i=$CH_3$, $CH_2$, and $H_2O$) of the k-th standard sample (k=BSA, DOPC, and water samples), and $C_{jk}$ is the volume concentration of the j-th component (j=protein, lipid, and water) of the k-th sample in the unit of volume fraction (ml/ml). For example, as illustrated in FIG. 8, the decomposition matrix is calculated from SRS intensity and concentration of water, protein calibration standard samples, and lipid calibration standard samples.

The inverse of decomposition matrix $M_{ij}^{-1}$ is interpreted as the SRS intensity of i-th Raman band measured from a pure material of the j-th component. $M_{ij}^{-1}$ can be broken down to the Raman cross-section of the molecule $\sigma_{ij}$ and the efficiency of the imaging system $A_{io}$ as optimized for the imaging of calibration standards:

$$M_{ij}^{-1} = \sigma_{ij} A_{i0} \quad \text{(Eq. 2)}$$

In some implementations, Eq. 2 enables the expression of the SRS signal of calibration standard samples as $S_{ik} = \Sigma_j \sigma_{ij} A_{i0} C_{jk}$. In other words, when $M_{ij}^{-1} = \sigma_{ij} A_{i0}$ (Eq. 2) is applied to the inverse relation of $M_{ij} = \Sigma_k C_{jk} S_{ik}^{-1}$, we obtain $S_{ik} = \Sigma_j \sigma_{ij} A_{i0} C_{jk}$.

Figure 9:
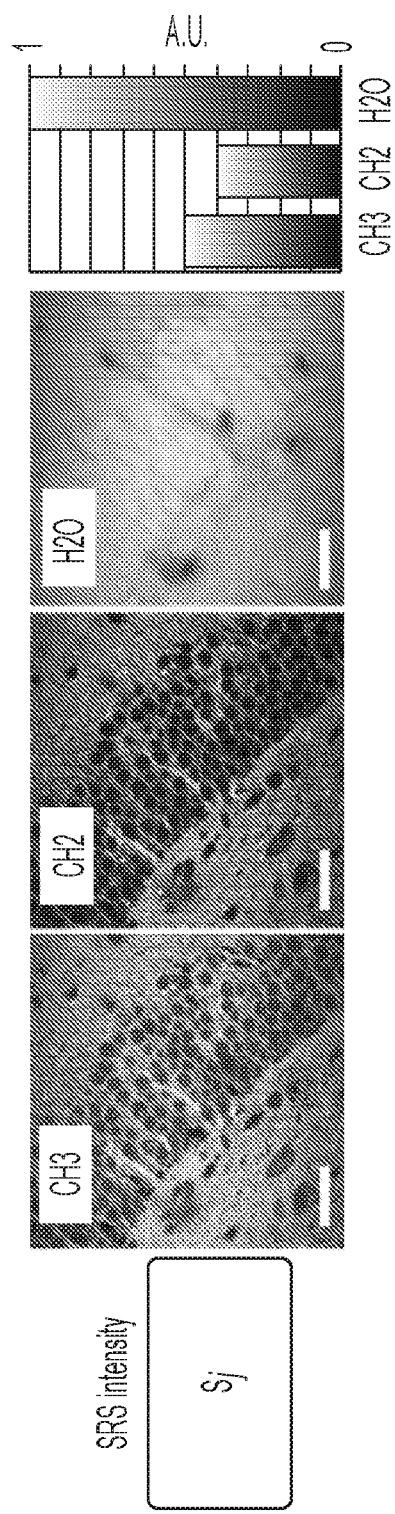
FIG. 9 illustrates the raw data showing SRS intensity image of mouse hippocampus at $CH_3$, $CH_2$, and $H_2O$ Raman bands, according to some implementations of the present disclosure.

The effect of sample light scattering in the spectral decomposition of sample images was analyzed. The SRS intensity images of a biological sample show intensity variation of both the abundance of the corresponding chemical groups and the attenuation by the sample, as the raw data illustrated in FIG. 9 showing SRS intensity image of mouse hippocampus at $CH_3$, $CH_2$, and $H_2O$ Raman bands, according to some implementations of the present disclosure. In FIG. 9, the scale bar is 40 μm. Spectral decomposition is processed by matrix multiplication of the decomposition matrix with SRS images at the $CH_3$, $CH_2$, and $H_2O$ Raman bands:

$$R_j(\vec{r}) := \Sigma_i M_{ij} S_i(\vec{r}) \quad \text{(Eq. 3)}$$

While the Raman cross-section $\sigma_{ij}$ is an intrinsic property of the chemical constituent, the efficiency of the microscope $A_{io}$ is affected by the optical aberration of the imaging system and/or the detector efficiency. When imaging samples, the light scattering and aberration caused by the sample introduces an extra attenuation factor $A_x(\vec{x})$ to the signal, which can be expressed as:

$$S_i(\vec{x}) = \Sigma_j \sigma_{ij} A_{i0} A_x(\vec{r}) C_j(\vec{r}) \quad \text{(Eq. 4)}$$

The sample induced attenuation factor is assumed to be independent of the Raman bands. Because of this sample induced attenuation factor, when spectral decomposition is applied to sample images, we do not get the true concentration by multiplying the decomposition matrix with the SRS intensity. Instead, the output of spectral decomposition is proportional to the concentration of the respective chemical components, and also to the spatially heterogeneous attenuation:

$$\Sigma_i M_{ij} S_i(\vec{r}) = A_x(\vec{r}) C_j(\vec{r}) \quad \text{(Eq. 5)}$$

Figure 10:
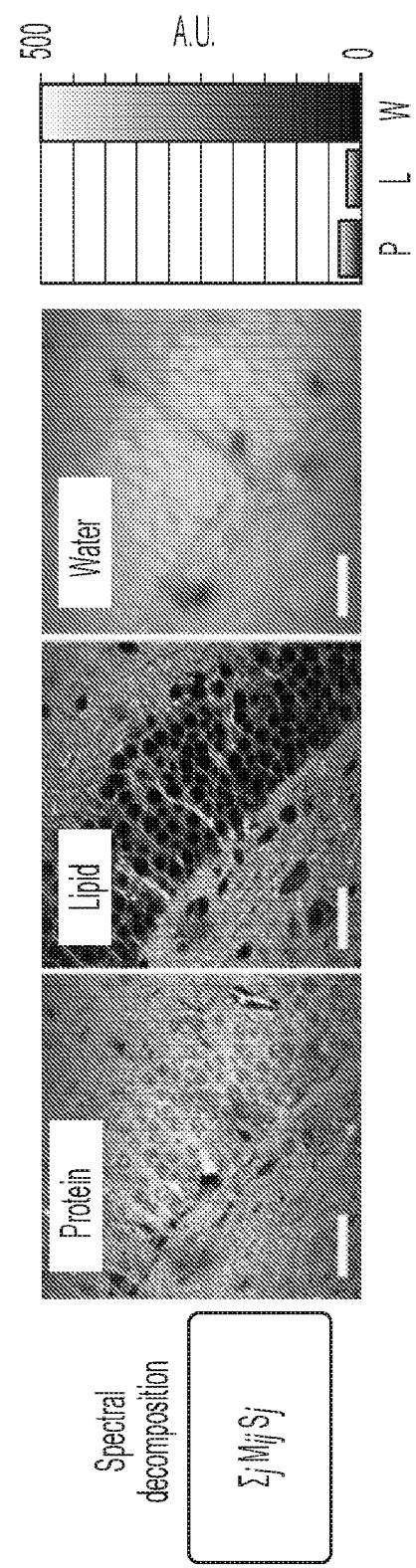
FIG. 10 illustrates the spectral decomposition of FIG. 9, according to some implementations of the present disclosure.

The spectral decomposition of FIG. 9 is also illustrated in FIG. 10, where P stands for protein, L stands for lipid, and W stands for water. The scale bar in FIG. 10 is 40 μm.

The attenuation factor varies with position, and with each sample. Thus, the attenuation factor limits the quantitative interpretation of spectral decomposition. However, the attenuation factor $A_x(\vec{r})$ can be calculated by making an approximation that the tissue is mostly composed of protein, lipid, and water. Thus, the sum of P/L/W volume fraction is 1 ml/ml, or:

$$\Sigma_j C_j = 1 \quad \text{(Eq. 6)}$$

where j=protein, lipid, and water (P/L/W in abbreviation). For this reason, referring back to Eq. 1, the decomposition matrix can be expressed using volume fractions. Under this assumption, the sum of spectral decomposition over P/L/W provides:

$$A_x(\vec{r}) = \Sigma_{ij} M_{ij} S_i(\vec{r})$$ (Eq. 7)

Figure 11:
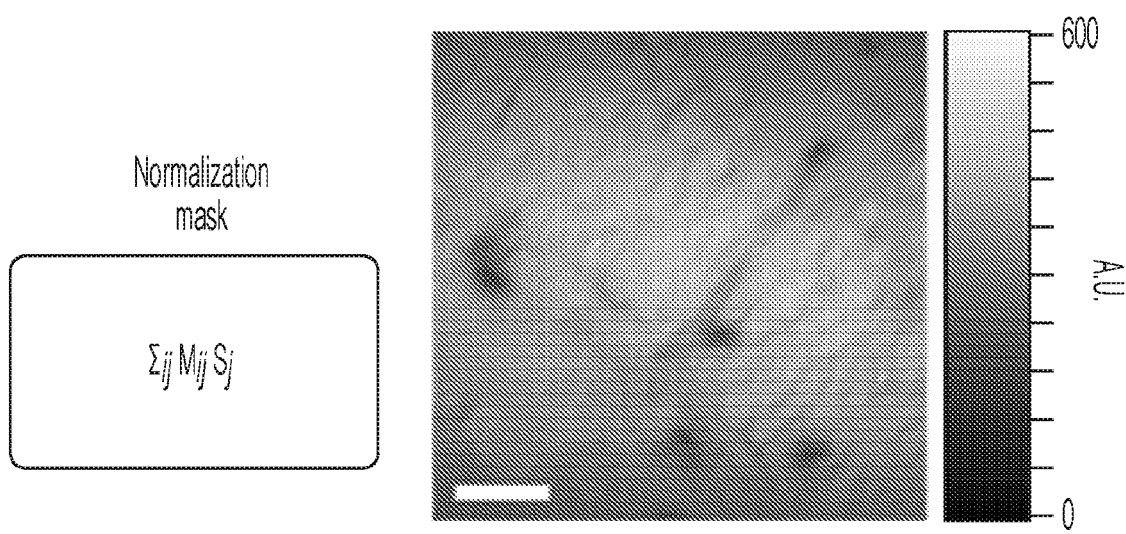
FIG. 11 illustrates the light scattering normalization mask calculated from the pixel-by-pixel sum of FIG. 10, according to some implementations of the present disclosure.

In some implementations, $A_x(\vec{r})$ is defined throughout the sample imaging volume, and serves as the normalization mask. For example, FIG. 11 illustrates the light scattering normalization mask calculated from the pixel-by-pixel sum of FIG. 10, according to some implementations of the present disclosure. The scale bar in FIG. 11 is 40 μm.

$A_x(\vec{r})$ measures the collective sample property that attenuates the SRS intensity at each voxel, which includes the presence of scatterers and/or absorbers above and below the imaging plane. Absolute concentration of P/L/W in volume fraction is obtained by dividing the spectral decomposition from Eq. 5 with the normalization mask:

$$C_j(\vec{r}) = \Sigma_i M_{ij} S_i(\vec{r}) / A_x(\vec{r}) = R_j(\vec{r}) / A_x(\vec{r})$$ (Eq. 8)

Figure 12:
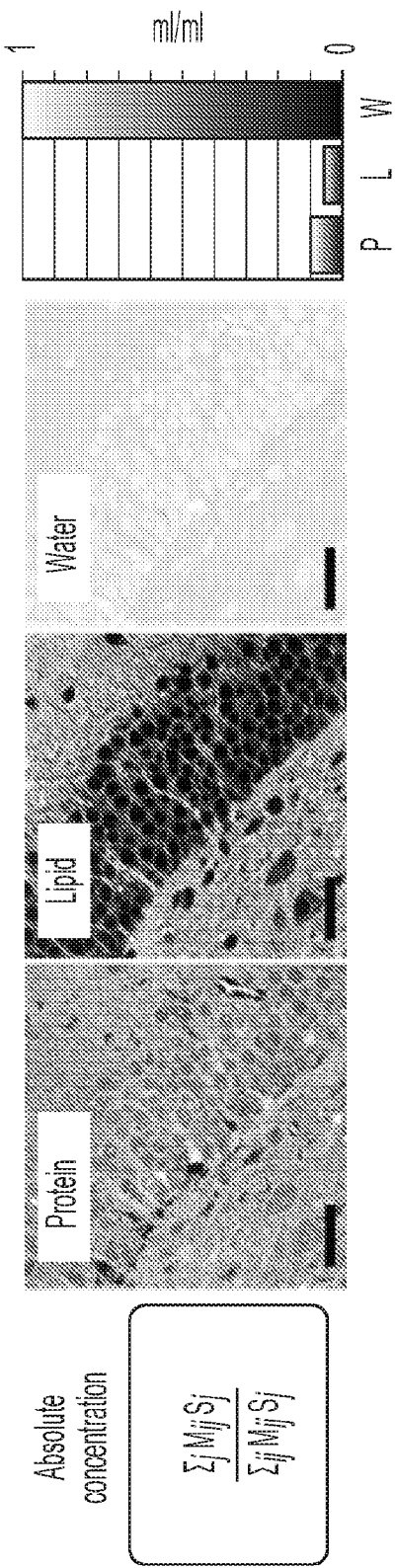
FIG. 12 illustrates the NoRI image of absolute concentration, according to some implementations of the present disclosure.

For example, FIG. 12 illustrates the NoRI image of absolute concentration obtained by dividing FIG. 10 with FIG. 11, where the concentration is measured as volume fraction in ml/ml. The scale bar in FIG. 12 is 40 μm.

Figure 13:
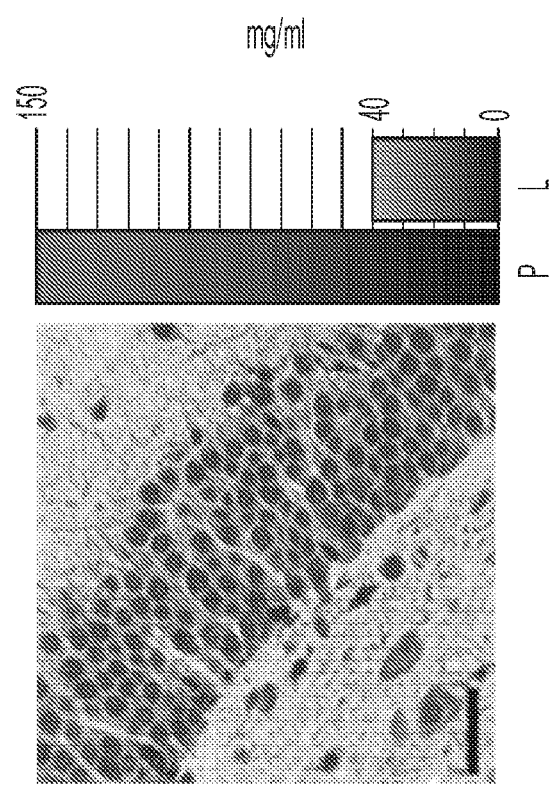
FIG. 13 illustrates the mass density of protein and lipid, according to some implementations of the present disclosure.

Mass concentration of protein and lipid can be estimated, by multiplying the volume fraction with the mass density of pure protein or lipids. For example, FIG. 13 illustrates the mass density of protein and lipid, according to some implementations of the present disclosure, where protein (P) and lipid (L) is calculated by multiplying volume fraction with the density ρ of pure protein or lipid. The scale bar in FIG. 13 is 40 μm. The present disclosure uses 1.364 g/ml and 1.0101 g/ml as representative density for protein and lipid, respectively. However, any representative value of density of pure protein or pure lipid can be used. For example, if the protein composition of a particular sample is such that a different mean protein density is representative, the mass density should be calculated using the different pure protein density.

Further, in some implementations, in addition to absolute P/L/W concentration, light scattering normalization can be applied to other Raman bands and/or raw SRS intensity data, thanks to the general nature of the linear relationship in Eq. 4.

Animal Protocols

Wild type mouse tissues are collected from 8-12 week male mice in accordance with the procedure approved by Institutional Animal Care and Use Committee (IACUC) at Harvard University. Transgenic female APP-PS1 mice and age-matched wild type (WT) female mice were purchased from Jackson Laboratory. All animal experiments were approved by the Institutional Animal Use and Care Committee at Massachusetts General Hospital. For live imaging of zebrafish embryo, AB strain wild type fish was used. All fish were kept at 28° C. on a 14-hour-light/10-hour-dark cycle. Embryos were collected from natural crosses. The chorion was removed manually prior to imaging. All fish-related procedures were carried out with the approval of Institutional Animal Care and Use Committee (IACUC) at Harvard University.

Test Results

Similar to FIGS. 6-13, the following description of test results is described in detail with reference to the components of the system 100 of FIG. 1.

To demonstrate the light scattering normalization in thick tissues, an xyz scan from a 90 μm thick section of mouse growth plate cartilage was acquired. For example, FIG. 14A illustrates the spectral decomposition showing a decrease of signal with imaging depth, according to some implementations of the present disclosure. The sample used for FIG. 14A is the rib growth plate cartilage of mouse on postnatal day 5. P is protein signal. L is lipid signal. The scale bar in FIG. 14A is 20 μm.

As shown, both raw SRS intensity and relative protein and lipid concentration obtained from spectral decomposition decrease with imaging depth. By contrast, NoRI provides an absolute concentration measurement that does not decrease with depth. For example, as shown in FIG. 14B, the NoRI image of protein and lipid mass density from FIG. 14A after light scattering normalization is illustrated, according to some implementations of the present disclosure, where the readout is absolute concentration in mg/ml and does not attenuate with imaging depth. The scale bar in FIG. 14B is 20 μm. The noise level of absolute concentration measurement increases when the raw SRS intensity decreases, as it would in the deep layer of a tissue. Imaging depth is limited by the detection sensitivity of SRS signals and varies with tissue types and optical clearing.

Figure 15:
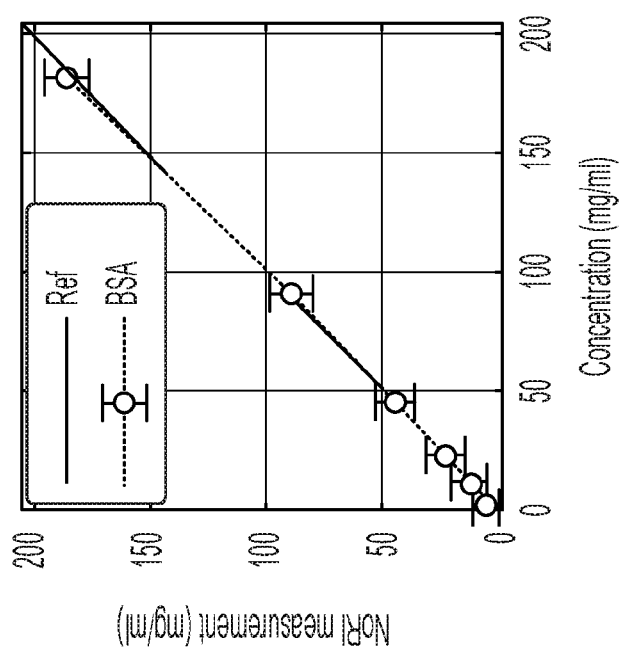
FIG. 15 illustrates the relationship between the protein concentration of BSA solution and NoRI measurement, according to some implementations of the present disclosure.

The accuracy of absolute concentration measurements by NoRI is validated by imaging bovine serum albumin (BSA) solutions of known concentrations. For example, FIG. 15 illustrates the relationship between the protein concentration of BSA solution and NoRI measurement, according to some implementations of the present disclosure. As shown, there is good agreement between the protein concentration of BSA solution and the NoRI measurement. The error bar in FIG. 15 is the standard deviation from all pixels in each image. Therefore, the NoRI measurement demonstrates excellent agreement with the actual concentration of solutions with sensitivity of approximately 15 mg/ml as measured by the standard deviation of protein concentration at each pixel within the image.

Figure 16:
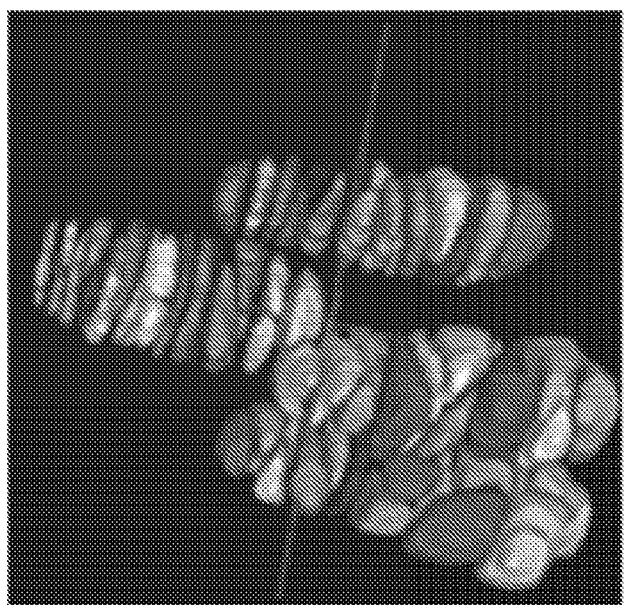
FIG. 16 illustrates the single cell 3D segmentation of chondrocytes in a mouse growth plate, according to some implementations of the present disclosure.

Further, in situ mass measurement was demonstrated by quantifying chondrocyte hypertrophy with NoRI. The growth plate of postnatal day five mouse was fixed and sectioned to 100 μm thickness for imaging. Individual cells were segmented in 3D. The protein density and the lipid density were integrated within each cell volume to calculate the total protein and the total lipid mass of single cells. For example, FIG. 16 illustrates the single cell 3D segmentation of chondrocytes in the mouse growth plate, according to some implementations of the present disclosure.

Figure 17:
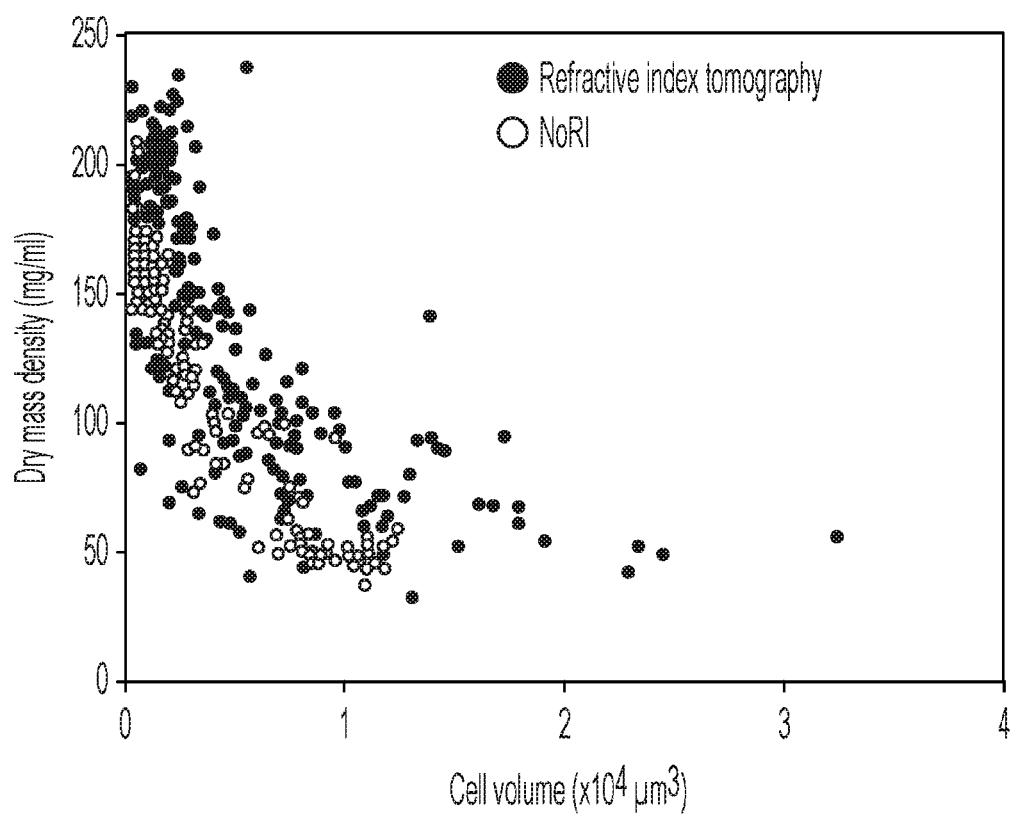
FIG. 17 illustrates the relationship between single cell volume and dry mass density of growth plate chondrocytes, according to some implementations of the present disclosure.

Because there is no existing technique to compare the protein mass and the lipid mass separately, the sum of protein and lipid mass density was compared with the dry mass density measured by refractive index tomography (using Tomocube, HT-2). The in situ measurement by NoRI shows good agreement with the measurement from dissociated chondrocytes, as illustrated in FIG. 17. The relationship between single cell volume and dry mass density of growth plate chondrocytes is shown, according to some implementations of the present disclosure. The scatter plot depicted in FIG. 17 shows that larger cells have lower mass density, where the NoRI data is acquired from a single thick tissue section, and refractive index tomography data is acquired from dissociated chondrocytes pooled from multiple animals.

Sample Preparations

Mouse tissues including brain, kidney, liver, pancreas, cartilage and skeletal muscle were dissected from the euthanized animal and immersion fixed in 4% formaldehyde in 4° C. for 24 hours. Mouse cerebellum was perfusion fixed with 4% formaldehyde in 4° C. for 24 hours.

Fixed tissues except for cartilage, along with APP-PS1 and WT brains are embedded in 2% agarose and sectioned to 40-100 µm thickness using a vibrating microtome (e.g., Precisionary Instruments, VF-300-0Z). Fixed brains were transferred into 30% sucrose at 4° C. until tissue sinks. Then the tissue was embedded in OCT and the OCT embedded frozen tissue blocks was sectioned into 25-µm slice in cryostat. The brain sections were washed of sucrose with phosphate buffered saline. Cartilage tissues were embedded in BSA-gelatin gel cured with formaldehyde in room temperature overnight, and sectioned by a vibrating microtome (e.g., Leica).

The tissue sections were transferred to phosphate buffered saline bath and stored in 4° C. until imaging. For imaging, a tissue section was sealed between a coverglass and a slide glass with phosphate buffered saline using a double-sided tape spacer (e.g., Grace Biolabs, SS1X13) and/or using a nail polish as sealant.

Application Examples

The present disclosure provides NoRI for measuring the absolute protein and lipid mass concentration of unlabeled cells, subcellular compartments, extracellular tissue, or any combination thereof. An analysis of a few cell and tissue types is included herein to highlight the range of potential applications of NoRI microscopy. For example, FIGS. 18A-27 generally illustrate in situ measurement of protein and lipid concentrations in various mouse tissues by NoRI. In some implementations, the samples were prepared using the techniques and/or methods disclosed herein.

Figure 18A:
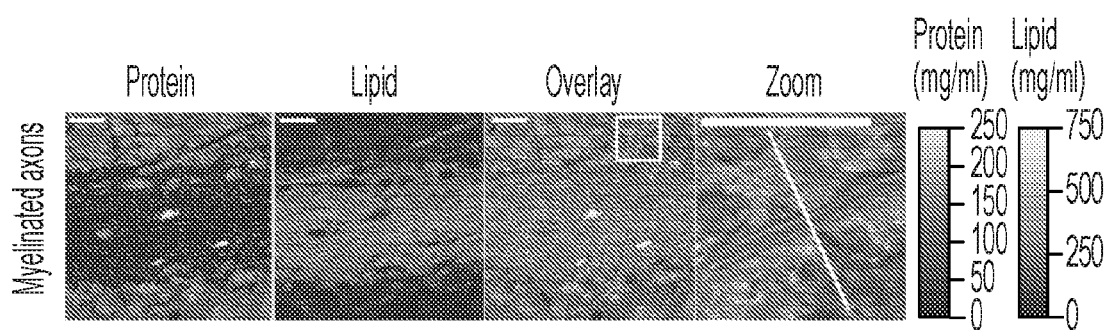
FIG. 18A illustrates myelinated axons in cerebellum, according to some implementations of the present disclosure.
Figure 18C:
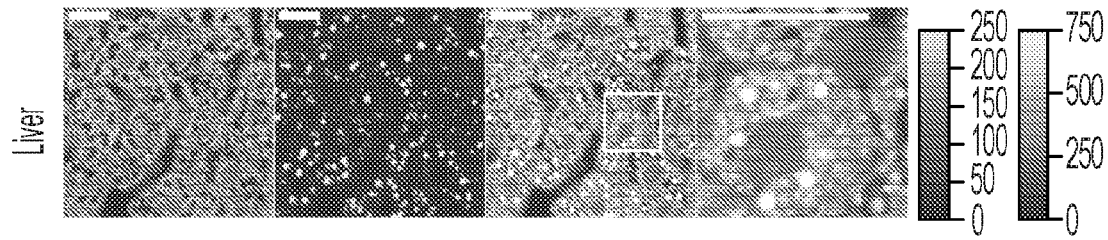
FIG. 18C illustrates hepatocytes containing large numbers of lipid droplets (LD), according to some implementations of the present disclosure.
Figures 19A, 19B, 19C:
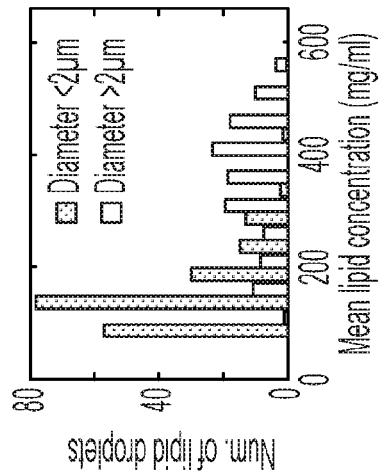
FIG. 19A illustrates the relationship of distance and lipid concentration of medullary tubules in kidney, according to some implementations of the present disclosure.
FIG. 19B illustrates the histogram of cytoplasmic lipid concentration in myofibers in FIG. 18B and additional images in the adjacent area, according to some implementations of the present disclosure.
FIG. 19C illustrates the histogram of mean lipid concentration of lipid droplets in FIG. 18C, according to some implementations of the present disclosure.

In some implementations, cells and organelles can be distinguished by the quantitative value of their distinctive protein and lipid concentrations. FIG. 18A illustrates myelinated axons in cerebellum, according to some implementations of the present disclosure, where the scale bar is 20 µm. FIG. 19A illustrates the relationship of distance and lipid concentration of medullary tubules in kidney, according to some implementations of the present disclosure, where the scale bar is 20 µm. FIG. 19C illustrates the histogram of mean lipid concentration of lipid droplets in FIG. 18C, according to some implementations of the present disclosure. As shown, myelin sheath (FIG. 18A and FIG. 19A) and lipid droplets in hepatocytes showed high lipid concentration over 200 mg/ml (FIG. 19C).

Figure 18B:
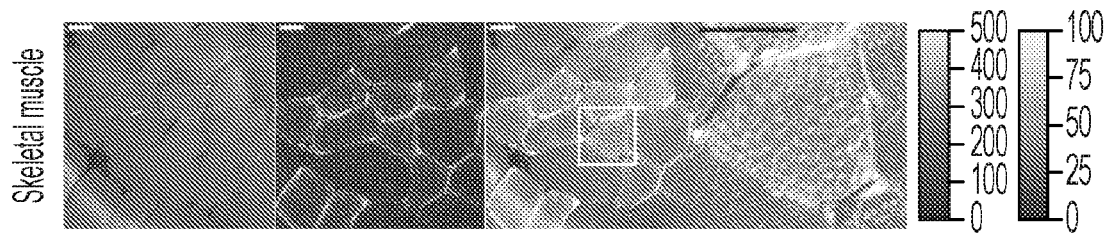
FIG. 18B illustrates transverse section of skeletal muscle showing fibers with high and low lipid content, according to some implementations of the present disclosure.

In addition, cytoplasmic lipid density, excluding lipid droplets, also showed variation with cell types. FIG. 18B illustrates transverse section of skeletal muscle showing fibers with high and low lipid content, according to some implementations of the present disclosure, where the scale bar is 20 µm. FIG. 19B illustrates the histogram of cytoplasmic lipid concentration in myofibers in FIG. 18B and additional images in the adjacent area, according to some implementations of the present disclosure. As shown, individual myofibers were recognizable by their distinct cytoplasmic lipid levels (FIG. 18B and FIG. 19B), even at much lower concentration around 10-30 mg/ml.

Figure 18D:
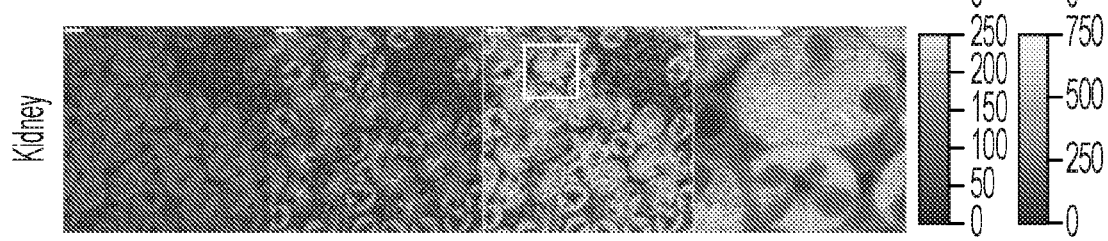
FIG. 18D illustrates the profile of lipid concentration across a single myelinated axon in FIG. 18A, according to some implementations of the present disclosure.

Turning now to FIG. 18D, the profile of lipid concentration across a single myelinated axon in FIG. 18A is illustrated, according to some implementations of the present disclosure, where the scale bar is 20 µm. As illustrated in FIG. 18D, kidney tubules also showed variation of cytoplasmic lipid density.

Figure 20:
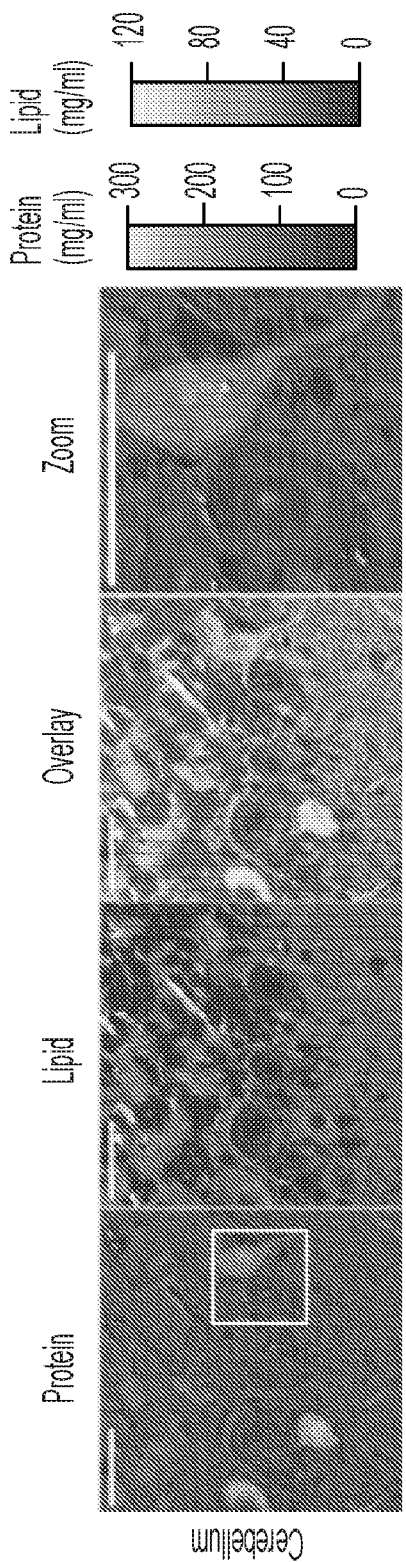
FIG. 20 illustrates examples of cell-to-cell variation in protein or lipid concentration, according to some implementations of the present disclosure.
Figure 21:
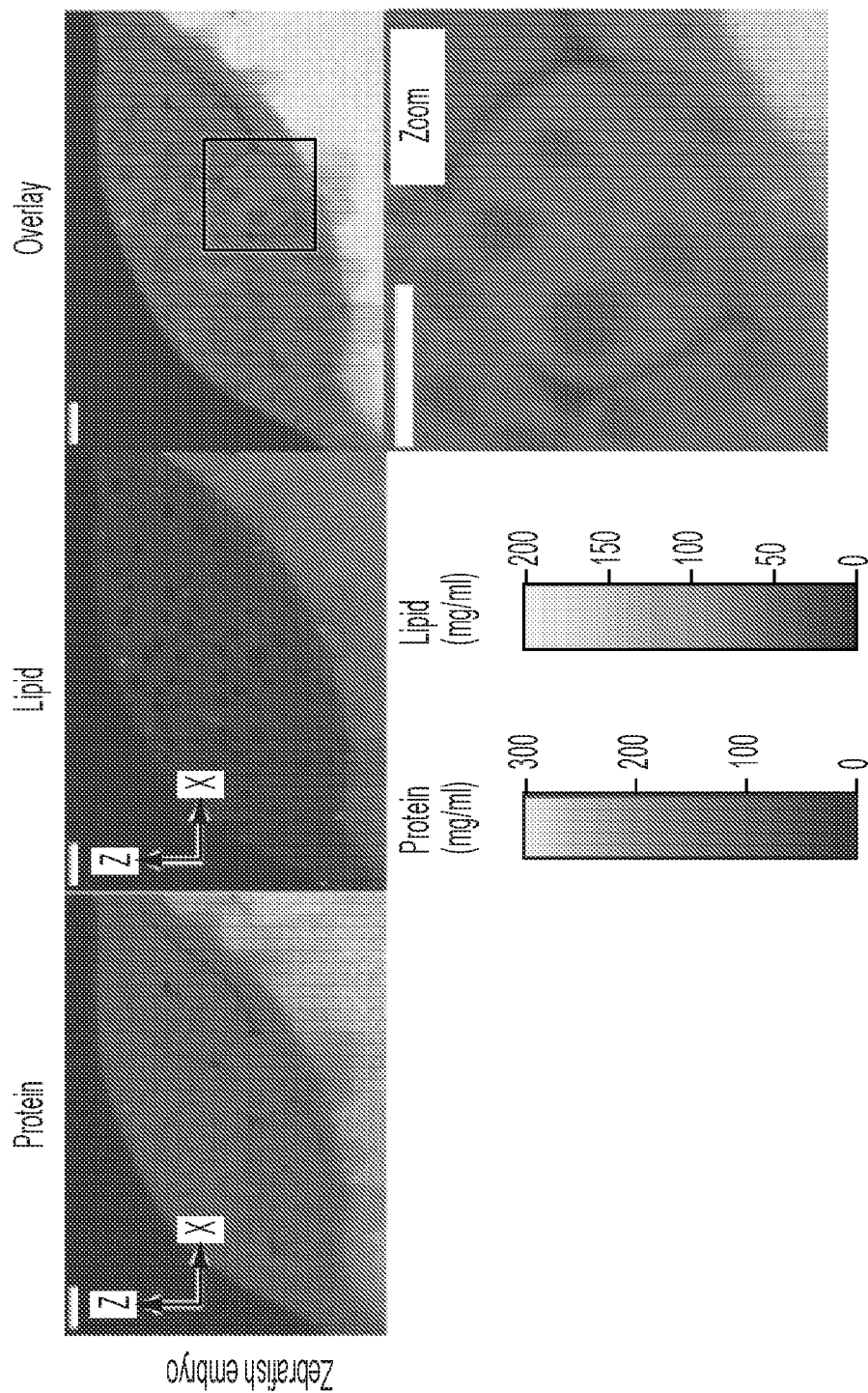
FIG. 21 illustrates the optical xz cross-section of live zebrafish embryo at 6 somite stage, according to some implementations of the present disclosure.
Figure 23:
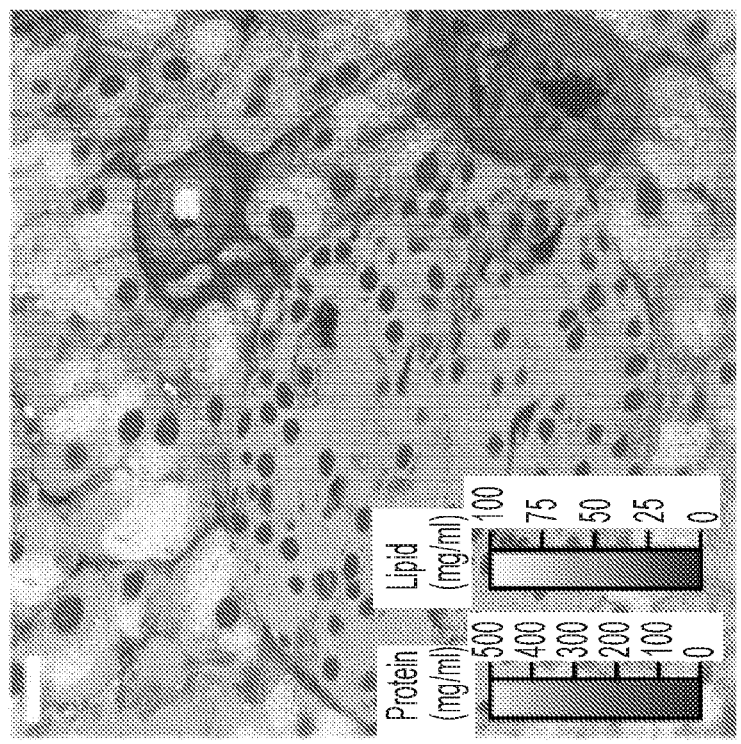
FIG. 23 illustrates the Mosaic image of pancreatic islet, according to some implementations of the present disclosure.

FIG. 18C illustrates hepatocytes containing large numbers of lipid droplets (LD), according to some implementations of the present disclosure, where the scale bar is 20 µm. FIG. 20, illustrates examples of cell-to-cell variation in protein or lipid concentration, according to some implementations of the present disclosure. FIG. 21 is a zoomed view of the notochord, showing the optical xz cross-section of live zebrafish embryo at 6 somite stage, according to some implementations of the present disclosure. FIG. 23 illustrates the Mosaic image of pancreatic islet, according to some implementations of the present disclosure, where the scale bar is 100 µm. As shown in FIG. 18C, FIG. 20, FIG. 21, and FIG. 23, cell nuclei are distinguished by the complete absence of lipid.

Turning now to FIG. 20, where examples of cell-to-cell variation in protein or lipid concentration is illustrated, the nucleoli showed higher protein concentration than nucleoplasm. Referring to FIG. 14B (showing the NoRI image of mouse growth plate cartilage) and FIG. 21 (showing the optical xz cross-section of live zebrafish embryo at 6 somite stage), non-cellular material such as extracellular matrix or yolk appeared to have characteristic protein and lipid concentrations.

In some implementations, protein and lipid concentration can vary even between cells of the same cell type (e.g., FIG. 20). Cerebellar Purkinje neurons showed greater than two-fold variation in protein concentration, in both cytoplasm and nucleoplasm. This variation is reproducible under varying conditions.

To demonstrate live imaging capability, live zebrafish embryo was imaged at six somite stage (e.g., FIG. 21). The protein and lipid concentrations at this stage did not vary much with different embryonic cell types. As expected, yolk granules are packed with proteins and lipids. Individual yolk granules could be recognized adjacent to the embryo, as they had lower protein and lipid concentrations, their stores having been partially depleted by the embryo.

Figure 22:
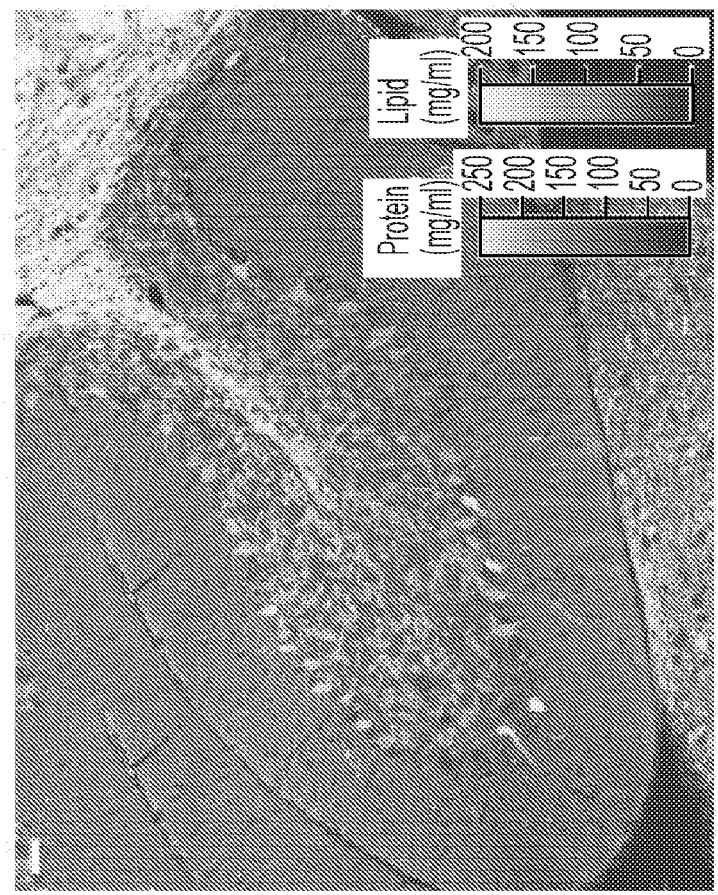
FIG. 22 illustrates the Mosaic image of lobe 10 of cerebellum from 5×4 images, according to some implementations of the present disclosure.

In some implementations, different concentration of protein and lipid can serve as image contrast for histological analysis. To demonstrate the potential for quantitative histology by NoRI, large area scans from mouse cerebellum and pancreas were acquired. For example, FIG. 22 illustrates the Mosaic image of lobe 10 of cerebellum from 5×4 images, according to some implementations of the present disclosure, where the scale bar is 100 µm; and FIG. 23 illustrates the Mosaic image of pancreatic islet, according to some implementations of the present disclosure. The time to image 1 cm×1 cm area was 6 hours at 60× magnification with 0.38 µm xy resolution and approximately 1.5 µm axial resolution; and 2 hours at 30× magnification at the cost of decreased axial resolution.

In addition, various known structures of cerebellum could be recognized. Large Purkinje neurons of various cytoplasmic concentration line between granular layer and molecular layer. The neuropil that is the tangled mass of submicroscopic dendrites and unmyelinated axons appear as diffuse matrix with relatively low protein and lipid concentrations in the molecular layer. Cells of the granular layer could be recognized by their compact nuclei. Dendritic glomeruli between the granular cells showed elevated lipid levels as expected from their dense membrane structure. White matter was marked by the high lipid content of myelin (e.g., FIG. 22).

NoRI image of the mouse pancreas also shows recognizable histological features. Acinar cells contained large number of high protein vesicles, which are likely zymogen granules for storing and secreting digestive enzymes. Protein dense membrane surrounds blood vessels and duct (e.g., FIG. 23).

Figure 24A:
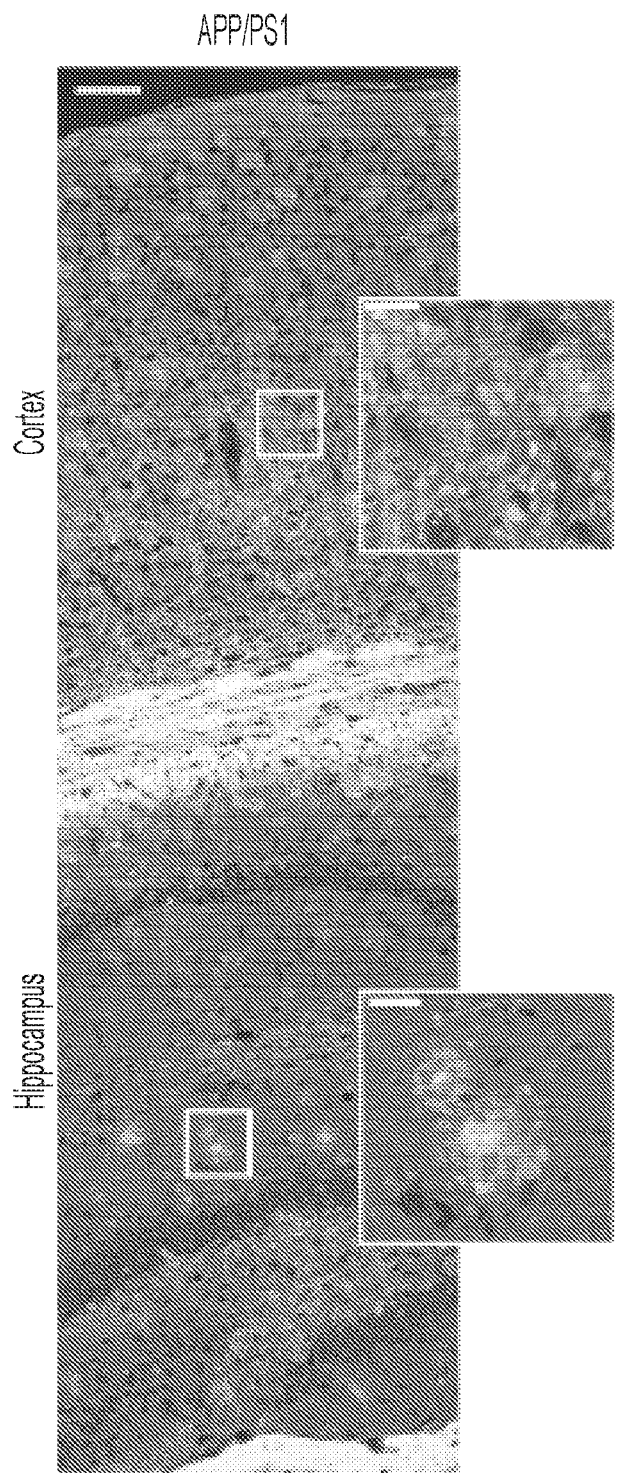
FIGS. 24A-24B illustrate the protein and lipid concentration images of APP/PS1 Alzheimer model and wild type mouse brains, according to some implementations of the present disclosure.
Figure 24B:
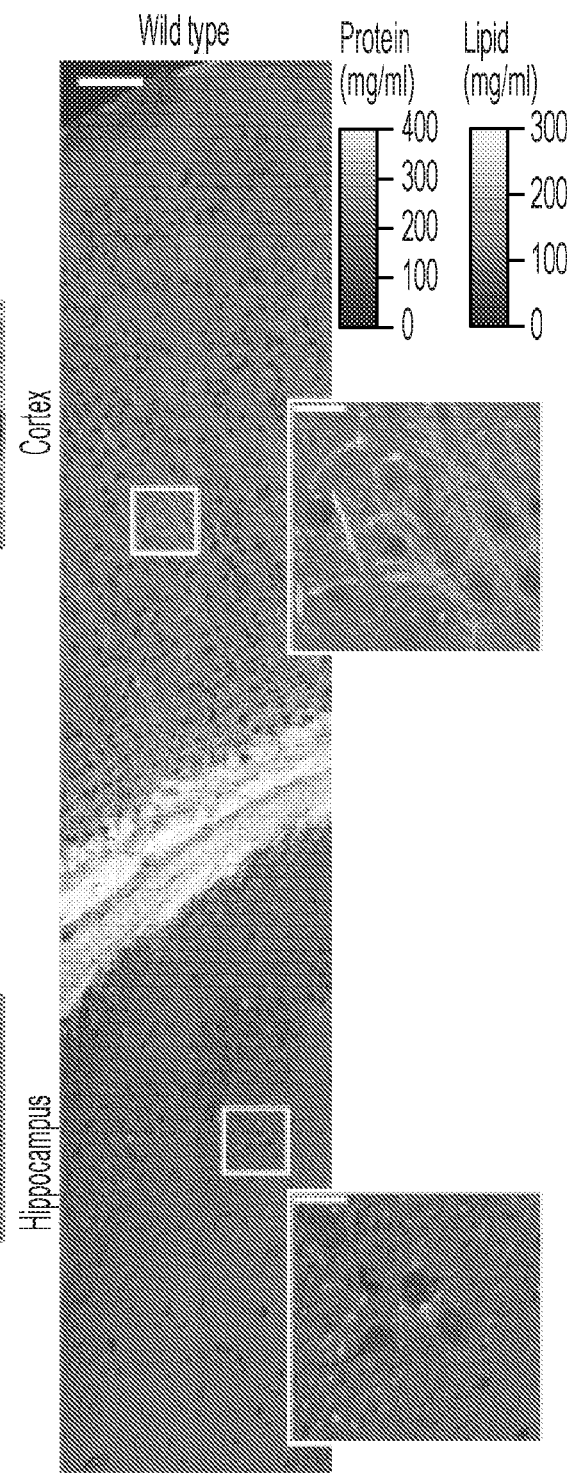

To demonstrate the utility of NoRI quantitative histology, the brain of an Alzheimer's disease model mouse was imaged (using APP-PS1). For example, FIGS. 24A-24B illustrate the protein and lipid concentration images of APP/PS1 Alzheimer model and wild type mouse brains, according to some implementations of the present disclosure, where the scale bar is 100 µm Compared to the normal histology, the APP-PS1 mouse brain showed large number of lesions in both protein and lipid images.

Figure 25:
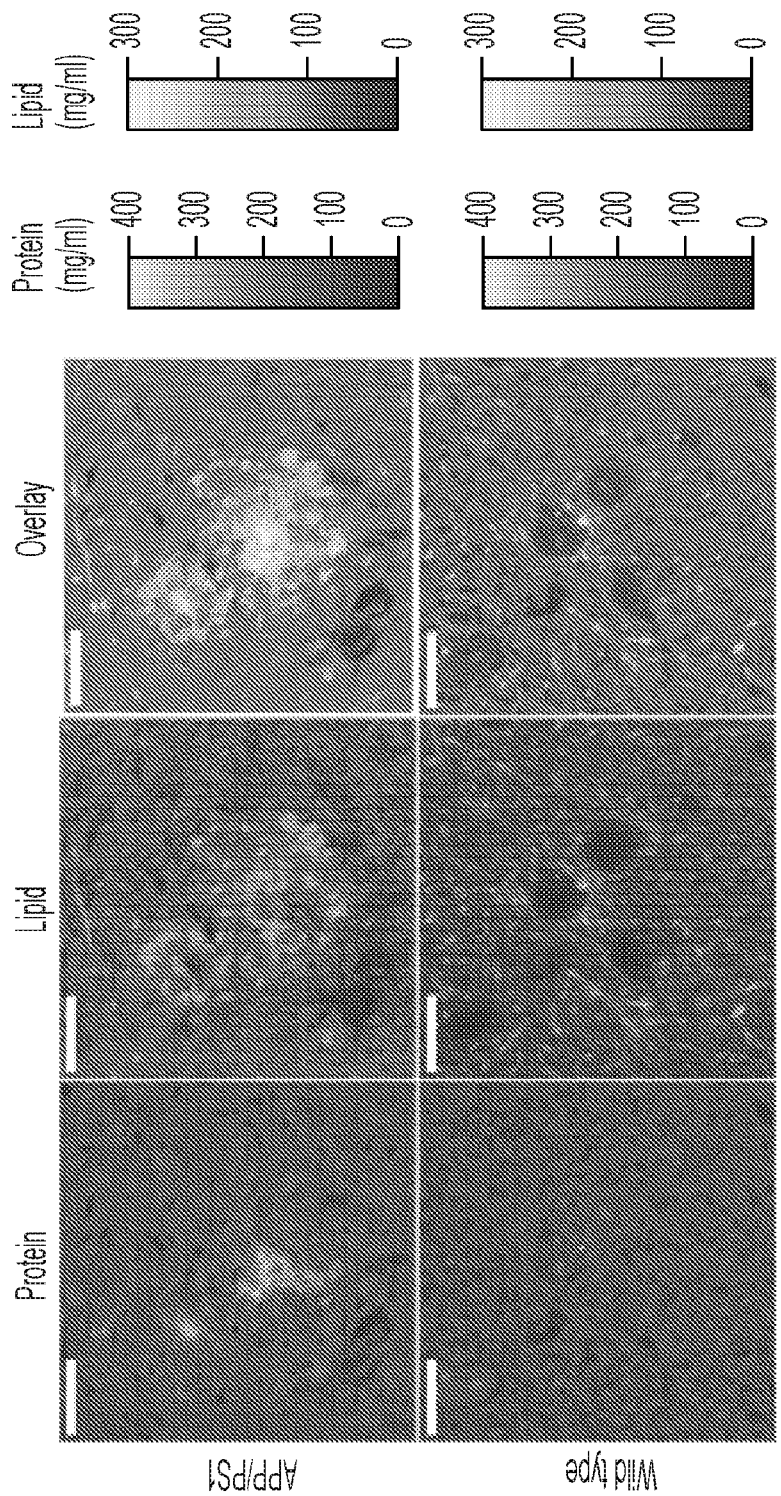
FIG. 25 illustrates the protein and lipid images from the insets in hippocampal areas in FIG. 23, according to some implementations of the present disclosure.

The protein image showed amyloid plaques in high protein concentration in the extracellular space, which were surrounded by patches of high lipid concentration. For example, FIG. 25 illustrates the protein and lipid images from the insets in hippocampal areas in FIG. 23, according to some implementations of the present disclosure, where the scale bar is 20 µm. The lipid rich patches were greater in number than amyloid plaques in the APP-PS1 mouse brain.

Figure 26B:
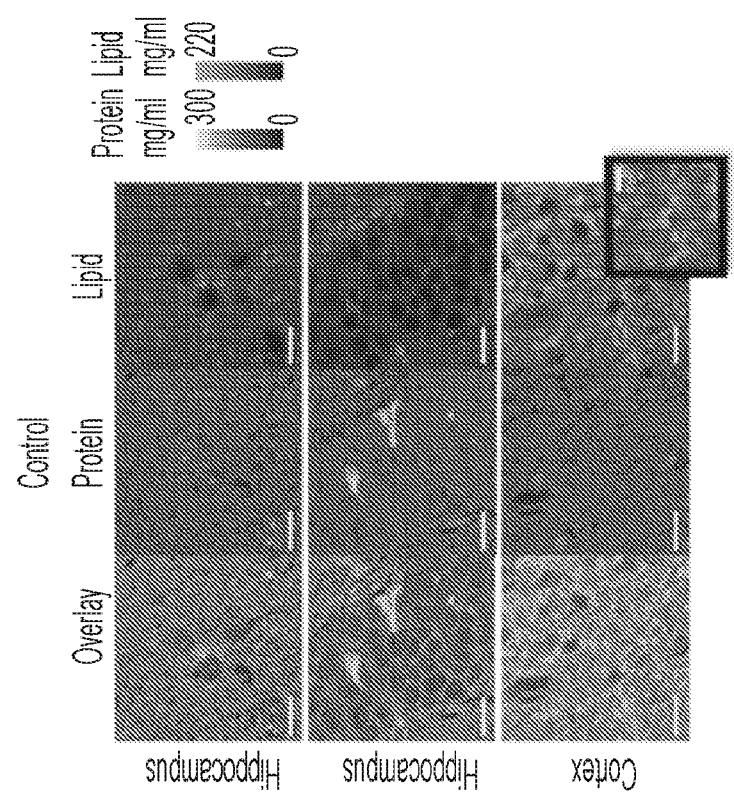
FIGS. 26A-26B illustrate the protein and lipid concentration images of APP-PS1 mouse brain and control mouse brain, according to some implementations of the present disclosure.
Figure 26A:
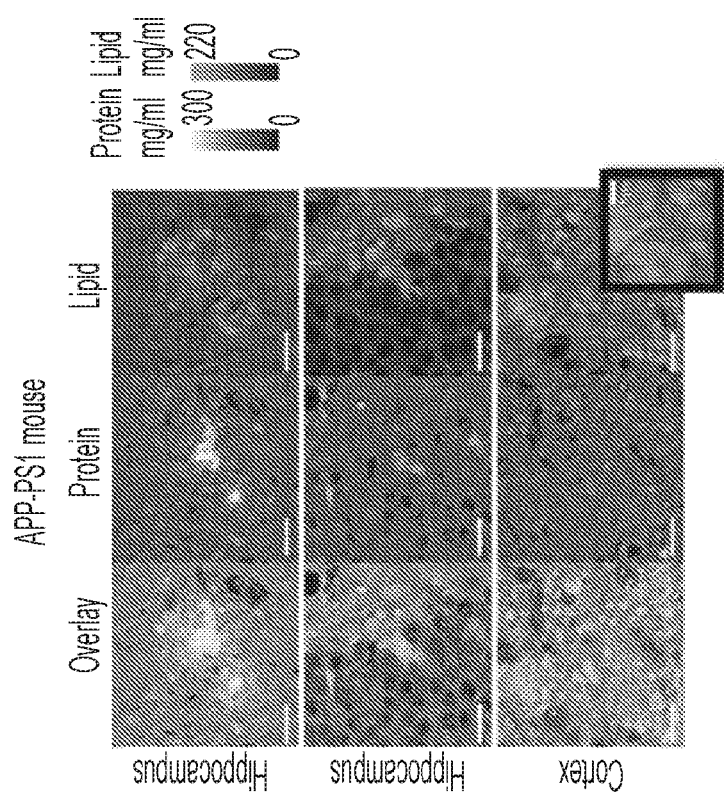

By contrast, higher protein concentrations were localized to nucleoli or the cell body in the wild type brain, and high lipid signal exclusively correlated with the myelin. For example, FIGS. 26A-26B illustrate the protein and lipid concentration images of APP-PS1 mouse brain and control mouse brain, according to some implementations of the present disclosure. The scale bar is 20 µm; and the inset scale bar is 5 µm.

Discussion

Under the following key assumptions and approximations, the absolute concentration measurement by NoRI is three-component spectral decomposition of NoRI places nucleic acids and polysaccharides into the protein fraction. By measuring additional Raman bands, it is possible to generalize NoRI to measure nucleic acids or polysaccharides in addition to proteins, lipids, and water.

Figure 27:
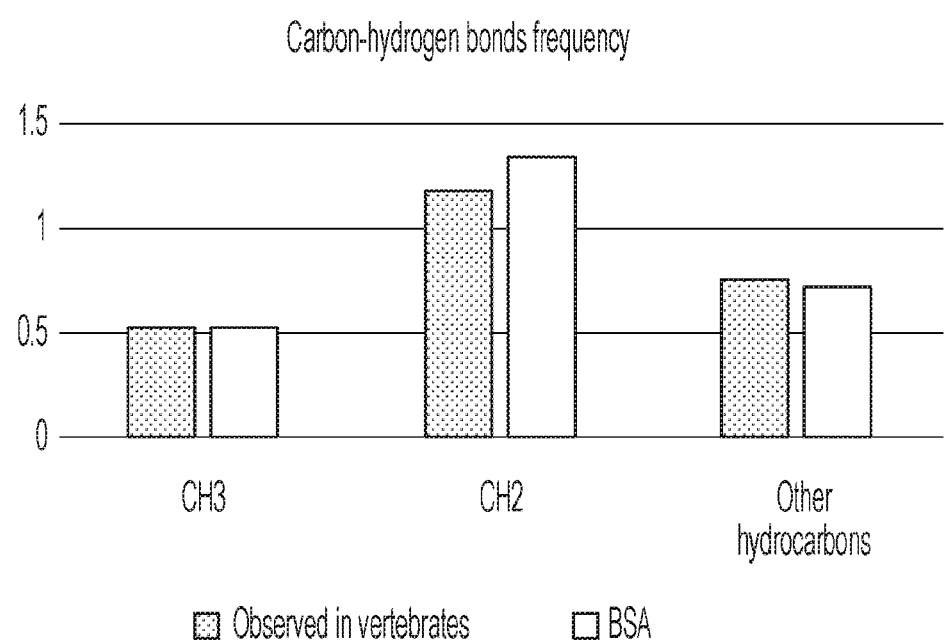
FIG. 27 illustrates the comparison of carbon-hydrogen bonds frequency in vertebrates and in bovine serum albumin (BSA), according to some implementations of the present disclosure.

Second, bovine serum albumin (BSA) is chosen as calibration standard for the protein Raman spectrum, because (i) it is economical and available in large quantity, (ii) it is easily dissolves in water, and (iii) it has a similar Raman spectrum in the $CH_2$ and $CH_3$ bands compared to the average vertebrate proteome. The majority of carbon-hydrogen (C—H) bonds of proteins are in the side chains. Therefore, the size of the $CH_2$ and $CH_3$ Raman band is determined by the average amino acid frequency of the proteome. The frequency of methyl groups, methylene groups and other hydrocarbons of BSA is very similar with that of average vertebrate proteome (see Table 1). The comparison of carbon-hydrogen bonds frequency in vertebrates and in bovine serum albumin (BSA) is also illustrated in FIG. 27, according to some implementations of the present disclosure.

TABLE 1

Frequency of methyl and methylene groups in bovine serum albumin and average vertebrate proteome

| Amino acids | Amino acids | $CH_3$ in side group | $CH_2$ in side group | Other C—H bonds | Observed Frequency in Vertebrates | Frequency in BSA |
|---|---|---|---|---|---|---|
| Alanine | A | 1 | | | 7.4% | 8.2% |
| Arginine | R | | 3 | | 4.2% | 4.4% |
| Asparagine | N | | 1 | | 4.4% | 2.4% |
| Aspartic Acid | D | | 1 | | 5.9% | 7.0% |
| Cysteine | C | | 1 | | 3.3% | 6.0% |
| Glutamic Acid | E | | 2 | | 5.8% | 0.0% |
| Glutamine | Q | | 2 | | 3.7% | 9.9% |
| Glycine | G | | | 1 | 7.4% | 2.9% |
| Histidine | H | | 1 | 2 | 2.9% | 2.7% |
| Isoleucine | I | 2 | 1 | 1 | 3.8% | 2.6% |
| Leucine | L | 2 | 1 | 1 | 7.6% | 11.1% |
| Lysine | K | | 4 | | 7.2% | 10.2% |
| Methionine | M | 1 | 2 | | 1.8% | 0.9% |
| Phenylalanine | F | | 1 | 5 | 4.0% | 5.1% |
| Proline | P | | 2 | | 5.0% | 4.8% |
| Serine | S | | 1 | | 8.1% | 5.5% |
| Threonine | T | 1 | | 1 | 6.2% | 5.8% |
| Tryptophan | W | | 1 | 5 | 1.3% | 0.5% |
| Tyrosine | Y | | 1 | 4 | 3.3% | 3.6% |
| Valine | V | 2 | | 1 | 6.8% | 6.5% | particularly accurate: (1) the tissue sample is made up of protein, lipid, and water; (2) the Raman spectra of BSA and DOPC is a good representation of the Raman spectra of the average proteome and lipidome of the sample; (3) wavelength dependency of optical aberration and light scattering is weak; and (4) absence of non-Raman processes.

First, a good approximation in many mammalian cells where the combined fraction of protein, lipid, and water is greater than 90% of the total chemical composition. Exceptions would occur in calcified tissue with high content of hydroxyapatite; bacterial cells with high content of nucleic acids; and cells that store large amount of polysaccharide. Polysaccharides and nucleic acids have a large number of carbon-hydrogen bonds which significantly overlaps with that of the $CH_3$ Raman band. As a result, the current Dioleoyl-phosphocholine (DOPC) is the most abundant lipid in cell membranes. DOPC's methyl and methylene group frequency is representative of a typical lipid with fatty acid chains. However, lipids without long carbon chains such as sterols have the $CH_2$ Raman band shifted from the position defined by DOPC. As a result, under the spectral decomposition scheme of the present disclosure, sterols are partially miscategorized to protein fraction, and the interpretation of lipid versus protein fraction should be done with this caution. Thus, it is also important to identify a Raman band to enable differential quantification of sterols from lipids with fatty acid chains.

Third, it can be assumed and/or approximated that the intensity attenuation caused by the sample light scattering does not change with the Raman bands. By using a nearinfrared light source, the intensity attenuation from tissue light scattering and absorption is indeed nearly independent of wavelength. The Stokes beam wavelength is fixed at 1045 nm, and the pump beam wavelength changes between 770 nm and 805 nm, to select different Raman bands. Reduced scattering coefficient of typical tissue in 770-805 nm is on the order of 2 mm$^{-1}$, and its change over 770-805 nm range is typically less than 0.5 mm$^{-1}$.

Hence, the length scale of tissue thickness by which light scattering property will show that significant (1/e) deviation between 770 and 805 nm is on the order of 2 mm. Because the SRS process requires a tight focus of light, the depth range for SRS signal detection is less than 200 μm, which is an order of magnitude smaller than the length scale of wavelength dependence of tissue light scattering. Optical clearing of the tissue can increase the imaging depth limit to several hundreds of microns, but the light scattering will decrease as well.

Fourth, SRS imaging is generally free of non-Raman background, compared to other nonlinear Raman imaging modalities. However, pigment molecules in the tissue, which absorb infrared light, will give rise to strong non-Raman signals, and may even damage the sample by heating. It was observed that hemoglobin in red blood cells has a strong non-Raman signal, which can result in erroneous absolute concentration output. On the other hand, infrared absorption by melanin in retinal pigmented epithelium or skin led to sample damage by burning, which was prevented by bleaching with hydrogen peroxide.

Benefits of the NoRI System

Compared to the existing methods for total protein and lipid quantification, NoRI's unique benefit is that absolute quantification can be done with high spatial resolution in intact tissues. Conventional quantification methods are either bulk assays (such as Bradford assay), or semi-quantitative approaches using dyes. Existing cutting-edge techniques such as refractive index tomography and suspended microchannel resonator can provide absolute mass measurement. But these are limited in the breadth of samples to which they can be applied, and cannot distinguish protein and lipid.

NoRI expands the technical capability for protein and lipid mass quantification by utilizing broadly applicable assumptions. NoRI can enable diverse research topics where the amount and distribution of protein and lipid mass is central, including and not limited to: cell growth, skeletal development, and neurodegenerative diseases.

For example, NoRI measurements of protein density may provide a label-free way to visualize condensation of proteins from liquid-liquid phase separation. The concentration of protein and lipid can serve as a histological marker. Unlike conventional histological images that may have different staining intensities from batch to batch, NoRI histology takes advantage of the protein and lipid concentrations, which are intrinsic properties of tissues that can be directly compared between different samples.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present disclosure, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively, or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Conclusion

One or more elements or aspects or steps, or any portion(s) thereof, from one or more of any of claims 1-22 below can be combined with one or more elements or aspects or steps, or any portion(s) thereof, from one or more of any of the other claims 1-22 or combinations thereof, to form one or more additional implementations and/or claims of the present disclosure.

While various examples of the present disclosure have been described above, it should be understood that they have been presented by way of example only, and not limitation. Numerous changes to the disclosed examples can be made in accordance with the disclosure herein without departing from the spirit or scope of the disclosure. Thus, the breadth and scope of the present disclosure should not be limited by any of the above described examples. Rather, the scope of the disclosure should be defined in accordance with the following claims and their equivalents.

Although the disclosure has been illustrated and described with respect to one or more implementations, equivalent alterations and modifications will occur to others skilled in the art upon the reading and understanding of this specification and the annexed drawings. In addition, while a particular feature of the disclosure may have been disclosed with respect to only one of several implementations, such feature may be combined with one or more other features of the other implementations as may be desired and advantageous for any given or particular application.

The terminology used herein is for the purpose of describing particular examples only and is not intended to be limiting of the disclosure. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this disclosure belongs. Furthermore, terms, such as those defined in commonly used dictionaries, should be interpreted as having a meaning that is consistent with their meaning in the context of the relevant art, and will not be interpreted in an idealized or overly formal sense unless expressly so defined herein.

What is claimed is:

1. A method for measuring a composition of a biological sample, the method comprising:
   receiving a stimulated Raman scattering (SRS) image of the biological sample from an optical detector;
   via a processor, computationally removing the effect of light scattering in the received SRS image by measuring attenuation of the received SRS image and applying an attenuation factor via a normalization mask to the SRS image; and determining an absolute concentration of total protein, total lipid, and/or water from the biological sample by the processor.

2. The method of claim 1, wherein the SRS image is received from a stimulated Raman scattering (SRS) microscopy.

3. The method of claim 1, further comprising:

based at least in part on the determined absolute concentration of the total protein, the total lipid, and/or the water from the biological sample, assessing a protein mass and/or a lipid mass of the biological sample.

4. The method of claim 3, wherein the protein mass and/or the lipid mass of the biological sample is assessed in situ.

5. A method for measuring a composition of a biological sample, the method comprising:

receiving a stimulated Raman scattering (SRS) image of the biological sample from an optical detector;

via a processor computationally removing the effect of light scattering in the received SRS image by measuring attenuation of the received SRS image and applying an attenuation factor via a normalization mask to the SRS image;

determining an absolute concentration of total protein, total lipid, and/or water from the biological sample via a processor;

acquiring SRS images at selected Raman bands;

determining an SRS intensity of each of the selected Raman bands; and mapping the determined SRS intensity of the each of the selected Raman bands to a corresponding protein, lipid, or water fraction.

6. The method of claim 5, further comprising applying background subtraction and/or flat field correction to the acquired SRS images.

7. The method of claim 5, wherein the selected Raman bands include a $CH_3$ Raman band, a $CH_2$ Raman band, an $H_2O$ Raman band, or any combination thereof.

8. The method of claim 5, wherein the Raman bands are selected from high-wavenumber region and/or fingerprint region.

9. The method of claim 5, wherein the mapping is accomplished through spectral decomposition.

10. The method of claim 9, wherein the spectral decomposition includes three or more spectral components.

11. The method of claim 5, further comprising:

determining a decomposition matrix from SRS intensity and concentration of calibration standard samples; and processing spectral decomposition by matrix multiplication of the determined decomposition matrix with the acquired SRS images.

12. The method of claim 11, wherein the decomposition matrix is determined by measuring the SRS intensity at $CH_3$, $CH_2$, and/or $H_2O$ bands of the calibration standard samples.

13. The method of claim 11, wherein the calibration standard samples include a protein solution, a lipid solution, water, or any combination thereof.

14. The method of claim 11, wherein the calibration standard samples are assembled into a single sample holder and imaged at a maximum intensity z position.

15. The method of claim 11, wherein output of the processing the spectral decomposition is proportional to a concentration of a respective chemical component.

16. The method of claim 11, wherein output of the processing the spectral decomposition is proportional to an attenuation due to light scattering.

17. The method of claim 16, wherein the stimulated Raman scattering (SRS) image is received from an optical system; and wherein the attenuation due to light scattering and/or imperfection of the optical system is spatially heterogeneous.

18. The method of claim 11, wherein the computationally removing the effect of light scattering in the received SRS image includes determining an attenuation to output a normalization mask; and wherein the determining the absolute concentration of the total protein, the total lipid, and/or the water from the biological sample includes dividing the processed spectral decomposition with the normalization mask.

19. The method of claim 18, wherein the normalization mask is determined from a pixel-by-pixel sum of the spectral decomposition.

20. The method of claim 18, further comprising:

estimating mass concentration of protein or lipid in the biological sample by multiplying the absolute concentration of the total protein or the total lipid with mass density of pure protein or pure lipid.

\* \* \* \* \*